US007510539B2

(12) United States Patent
Katane et al.

(10) Patent No.: US 7,510,539 B2
(45) **Date of Patent: *Mar. 31, 2009**

(54) HEALTH EQUIPMENT

(75) Inventors: Fumio Katane, Koshigaya (JP); Hideaki Sakitsu, Taitou-ku (JP)

(73) Assignee: Protec House Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/909,451

(22) Filed: Aug. 2, 2004

(65) Prior Publication Data

US 2005/0020953 A1 Jan. 27, 2005

Related U.S. Application Data

(62) Division of application No. 09/646,503, filed as application No. PCT/JP00/00189 on Jan. 18, 2000, now Pat. No. 6,790,194.

(30) Foreign Application Priority Data

Jan. 18, 1999 (JP) ....................................... 11-882
Jul. 13, 1999 (JP) ................................ 11-199632

(51) Int. Cl.
*A61F 5/00* (2006.01)

(52) U.S. Cl. .............................. 602/36; 602/32; 602/38

(58) Field of Classification Search ................... 602/36, 602/19, 32, 38, 5, 20; 606/237, 241; 482/904, 482/142, 95, 143, 907
See application file for complete search history.

(56) References Cited

U.S. PATENT DOCUMENTS 951,560 A * 3/1910 Eaton .......................... 602/32
1,356,365 A * 10/1920 Hosmer ....................... 602/32
1,527,754 A * 2/1925 Simon ......................... 601/24
2,183,265 A * 12/1939 Maloney ...................... 482/95
2,274,574 A * 2/1942 Zerne ......................... 482/129
2,633,125 A * 3/1953 Yellin .......................... 602/36
3,640,571 A * 2/1972 Keropian .................... 297/464
4,531,514 A * 7/1985 McDonald et al. .......... 606/241
4,813,746 A * 3/1989 Mulholland ................. 297/488
4,903,355 A * 2/1990 Hickerson ..................... 5/83.1
4,999,862 A * 3/1991 Hefty ........................... 5/87.1
5,031,605 A * 7/1991 Mills ........................... 602/36
5,165,123 A * 11/1992 Colpron ........................ 5/83.1
5,290,219 A * 3/1994 Hetrick ........................ 602/32

(Continued)

*Primary Examiner*—Patricia M Bianco
*Assistant Examiner*—Michael A. Brown
(74) *Attorney, Agent, or Firm*—Jordan and Hamburg LLP

(57) ABSTRACT

Health equipment for dragging the lumber with the trunk of the human body securely supported is provided. The trunk support 2 is bendable only inwardly, and holds and supports the trunk of the human body. Since the trunk support 2 is placed around the human body and enfolds from the area below the costae to above the pelvis, the human body is securely supported, whereby lumbago treatment can be carried out with the patient suspended in the air. Since the lumber is dragged with the weight of the lower part of the patient's body, there is no possibility that the lumber is dragged with the excessive weight. The leg hanging unit 4 is a device to hang the legs of the patient. By using this leg hanging unit 4, so called mobilization may be carried out with the lower back portion suspended in the air, thereby increasing effectiveness of lumbago treatment.

21 Claims, 22 Drawing Sheets

U.S. PATENT DOCUMENTS 5,303,716 A * 4/1994 Mason et al. ................. 601/34
5,333,333 A * 8/1994 Mah ............................. 5/87.1
5,366,277 A * 11/1994 Tremblay ................... 297/464
5,379,468 A * 1/1995 Cassidy et al. ................ 5/86.1
5,380,269 A * 1/1995 Urso ........................... 602/19
5,387,186 A * 2/1995 Edland ........................ 602/36
5,447,356 A * 9/1995 Snijders ................... 297/284.3
5,501,656 A * 3/1996 Homma et al. ................ 601/33
5,651,149 A * 7/1997 Garman ...................... 5/81.1 R
5,651,764 A * 7/1997 Chiu ........................... 602/36
6,213,558 B1 * 4/2001 Axelson et al. ............. 297/464
6,368,296 B1 * 4/2002 Eiter et al. .................... 602/19
6,513,824 B2 * 2/2003 DuBose ................... 280/304.1
6,679,510 B2 * 1/2004 Perena .................... 280/250.1
6,790,194 B1 * 9/2004 Katane et al. ................. 602/36

* cited by examiner

HEALTH EQUIPMENT

TECHNICAL FIELD

The present invention relates to health equipment for supporting the trunk of the human body and dragging his or her lumber with the weight of the lower part of the body.

BACKGROUND ART

In general, a bed for lumbago treatment comprising a bed for letting the patient lie, a fixing belt for fixing the patient on the bed, ankle belts for attaching around the ankles of the patient, and a weight being hanged from the ankle belts is known. In a bed for lumbago treatment of this type, the crooked spinal column is straightened while dragging the lower part of the back with a weight to treat lumbago.

However, in a bed of this type, since the lower part of the back is dragged with the patient lain, the movement of the patient under treatment is limited, and the patient needs an assist from somebody else to attach the belt, thereby requiring significant labor costs. Although the dragging weight is adjusted based on the experience of the doctor or the physical therapist, it could be too heavy or too light, and thus it is troublesome to adjust. In addition, it has been necessary to allocate a significant space for installing the bed.

Accordingly, it is an object of the present invention to provide health equipment that can overcome all the problems in the related art described above, in other words, to provide epoch-making health equipment that can stably secure the trunk of the human body in the seated posture and drag the lumber by the weight of the lower part of the body.

DISCLOSURE OF INVENTION

The present invention provides health equipment for supporting the trunk of the user (patient) and dragging the lumber with the weight of the lower part of his/her body, comprising an equipment body, a freely deformable trunk supporting means mounted to the equipment body for supporting the trunk of the user by holding it from both sides of the body, and a seat portion on which the user sits.

The equipment body is a member that constitute a base on which the trunk supporting means is mounted. The trunk supporting means is characterized in being freely deformable. The seat portion may be formed of, for example, a chair separate from the equipment body. The seat portion may be integrated with the equipment body and formed in a chair having a seat back as a whole.

In the apparatus for lumbago treatment of the present invention, lumbago treatment may be easily executed by the following procedure. The user sits on the seat portion and takes a seated posture, and then places the trunk supporting means around his/her trunk while keeping the seated posture. At this time, it is preferable that the height of the seating portion is adjusted so that the trunk of the patient is at almost the same level as the trunk supporting means. Since the trunk supporting means is freely deformable, it can tight fit and hold the trunk of the patient securely.

Then the sitting portion is lowered or removed from the position where the user is sitting to allow the hip of the user to be suspended in the air, so that the lumber is dragged by the weight of the lower part of the body to treat the lumbago. In this situation, since the trunk of the body is supported by the trunk supporting means, a dragging force is not applied to the bones other than the lumber (for example the spinal column), whereby only the lumber area is dragged intensively, and effective lumbago treatment can be expected.

In order to adjust the height of the seating portion as described above, a mechanism to move the seating portion upward and downward must be provided. It is also possible to change the position of the user from the seated position to the position where the hip is suspended in the air by employing the structure wherein the seat portion is fixed and the trunk supporting portion is movable in the vertical direction. In other words, it is essential only that the trunk supporting means and the seat portion be relative movable in the vertical direction.

It is also possible to change the position of the user from the seated position to the position where the hip is suspended in the air by employing the structure in which the seat portion can be removed from the position where the user is sitting.

In the case where the trunk supporting means and the seat portion are constructed to be relatively movable in the vertical direction, a load applied to the lumber can be adjusted as desired by adjusting the distance of movement. In other words, no load is applied to the user's lumber when he or she is taking a seated posture on the seat portion, and a load applied to his or her lumber increases as the seat portion is lowered with respect to the hip of the user, and the load applied to his or her lumber becomes maximum when the hip of the user comes out of contact with the seat portion completely.

In order to make the load applied to the lumber adjustable based on the objective data, weight detecting means for detecting the weight of the user applied to the seat portion may be provided. The load increases in inverse proportion to the weight of the user which is applied to the seat portion. Therefore, the load applied to the lumber may be adjusted based on the weight data detected by the weight detecting means.

In the present invention of such an arrangement, the trunk supporting means may include a trunk supporting arm comprising a plurality of supporting members rotatably linked with respect to each other. In this arrangement, the trunk supporting means becomes freely deformable (in this structure, freely bendable), thereby creating the state where it fits around the trunk of the human and supports the same securely.

The trunk supporting arm is preferably formed so that the height is decreased in stages from the supporting member that supports the back of the human body to the supporting member that supports the belly of the human body. Therefore, the pressure applied onto the belly may be decreased.

The trunk supporting means may be constructed in such a manner that a pliant human body protecting member is mounted on the inner side of the trunk supporting arm, and a trunk supporting arm and the human body protecting member are covered by a covering member, and a non-slip member that is formed of a material being of a high contact resistance is attached on the inner surface of the covering member. In this arrangement, the trunk of the user may be softly enfolded by the human body protecting member, whereby the comfortable lumbago treatment may be carried out. In addition, the non-slip member may prevent the human body from being slipped with respect to the trunk supporting means, so that the proper state of supporting the trunk may be maintained.

In this arrangement, the human protecting member is preferably thicker at least in the area that supports the belly of the human body than that of other area in order to reduce the pressure applied to the belly of the human body.

By providing heating means for heating up the trunk of the user in the trunk supporting means, the thermal treatment for the lower part of the back as well as dragging treatment of the lumber may be carried out simultaneously, whereby further preferable effectiveness of treatment may be expected. By providing low frequency generating means that transmits low frequency to the trunk of the user in the trunk supporting means, low frequency treatment for the lower part of the back as well as dragging treatment of the lumber may be carried out simultaneously.

In addition to the components described above, health equipment of the present invention may include leg hanging means that holds the legs of the user in hanged state. The leg hanging means comprises, for example, a support, a string body hanged from the supporting body via a pulley, a leg holder mounted to the lower end of the string body for holding the legs of the user, wherein the height of the leg holder may be adjusted by manipulating the string body.

The leg hanging means is used for raising the knees or the ankles of the user upwardly. By raising the knees or ankles upwardly with the trunk of the human supported by the trunk supporting means, and turning the hanged legs toward right and left, a twisting action is applied to the lumber so that further effective treatment may be carried out for the lumber.

By constructing the leg hanging means in such a manner that the position thereof with respect to the user is adjustable in the front and back directions, the leg hanging means can be located at the proper position according to the length of the user's legs. It is also possible to provide a pair of unit each comprising a pulley, a string body, and a leg holder in order to hang the right leg and the left leg separately. In this arrangement, the various stimulations may be applied to the lumber by hanging the respective legs at different levels or by moving the respective legs alternately.

In health equipment of the present invention, there may be provided leg exercising means for moving the legs of the user upward and downward. The leg exercising means may comprise, for example, a leg supporting portion installed forward of the equipment body for supporting the legs of the user, and a raising/lowering mechanism for raising and lowering the leg supporting portion.

The leg exercising means is used for applying a proper stimulation to the lumber by allowing the legs of the user to move up and down in order to increase the effectiveness of treatment of the lumber. For example, the lumber may be adequately stimulated by placing the knees or ankles of the use on the leg supporting portion and moving the legs upward and downward by the raising/lowering mechanism.

By constructing the leg exercising means in such a manner that two leg supporting portions are provided and the leg supporting portion is moved upward and downward simultaneously or alternately by the raising/lowering mechanism, the left leg and the right leg may be moved up and down independently, so that the various stimulation may be applied to the lumber.

Health equipment of the present invention may be provided with cervical vertebrae dragging means for dragging the cervical vertebrae with the chin of the user held. The cervical vertebrae dragging means may comprise, for example a supporting body, a string body hanged from the supporting body via a pulley, a chin holder attached to the end of the string body for holding chin of the user, and a weight applying mechanism for applying a tensile load to the proximal portion of the string body.

The cervical vertebrae dragging means is effective for treatment of troubles in relation to the cervical vertebrae, such as whiplash injury or stiff shoulder. After the user attaches the chin holder on his or her chin, his or her chin is adequately dragged up by the weight applying mechanism, whereby the cervical vertebrae is dragged.

Health equipment of the present invention may be provided with a shoulder hanging means for holding the shoulder of the user. The shoulder hanging means comprises a supporting body, a string body hanged from the supporting body, and a shoulder holder attached on the lower end of the string body.

The shoulder hanging means has a miscellaneous function to prevent the body of the user being supported by the trunk supporting means and suspended in the air from slipping down. In other words, holding the shoulder of the user by the shoulder holder and creating the state of being suspended by the string body reliably prevent the body of the user from slipping down.

Health equipment of the present invention may be provided with rehabilitation means for doing pulling exercise using the user's arms, legs, and the upper part of the body. The rehabilitation means may be, for example, provided with a supporting body, a string body hanged from the supporting body via a pulley, an operating portion attached to the end portion of the string, and a resistance mechanism for applying a proper resistance force against the pulling operation of the operating portion.

The rehabilitation means can be used for doing exercise for example of the arms against the moderate resistance force applied by the resistance mechanism by gripping the operating portion and repeating the pulling operation, which contributes to the recovery of the muscular strength.

BEST MODE FOR CARRYING OUT THE INVENTION

Figure 1:
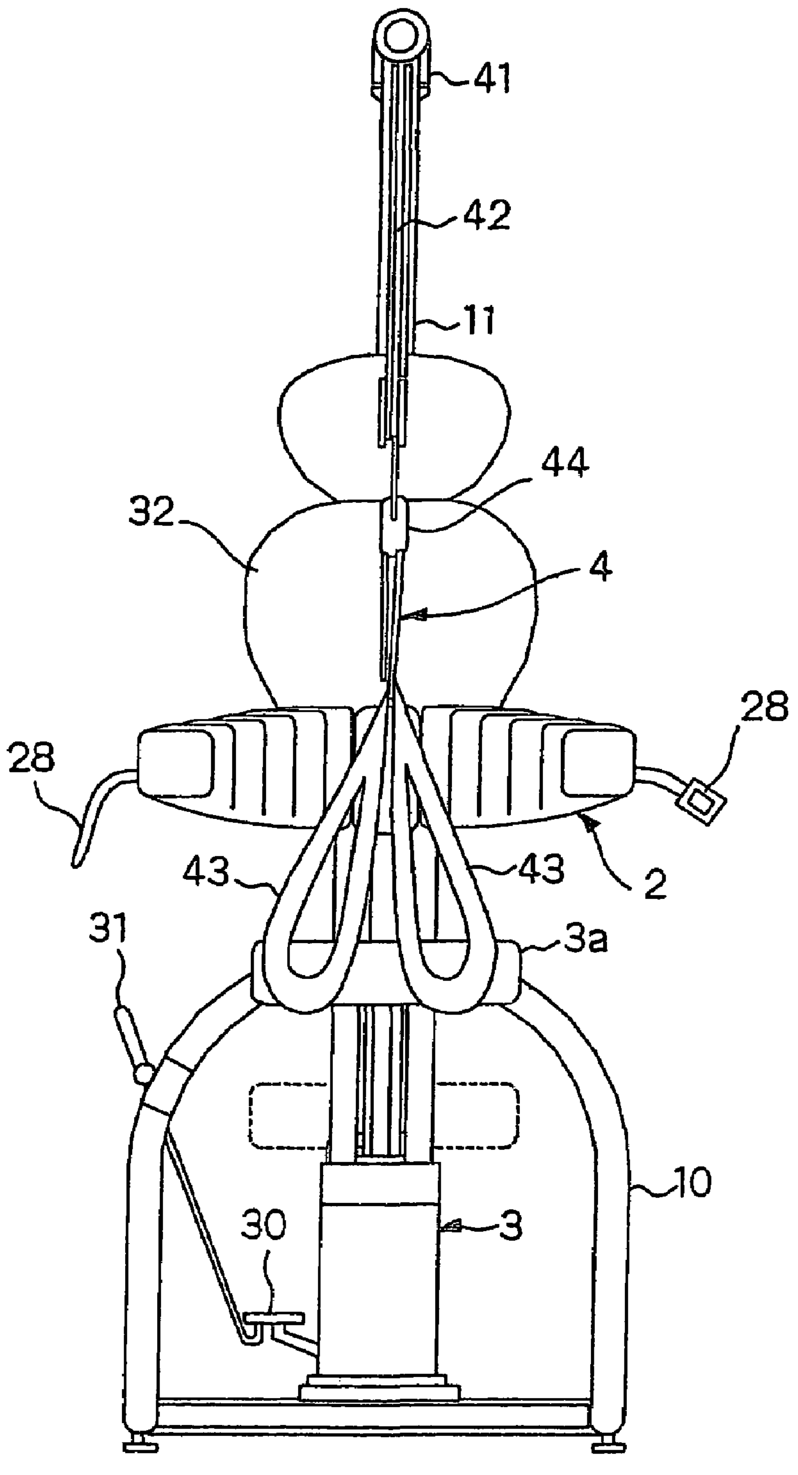
FIG. 1 is a front view of health equipment according to the first embodiment of the present invention.

Referring now to the drawings, the preferred embodiments of the present invention will be described.

First Embodiment

Figure 2:
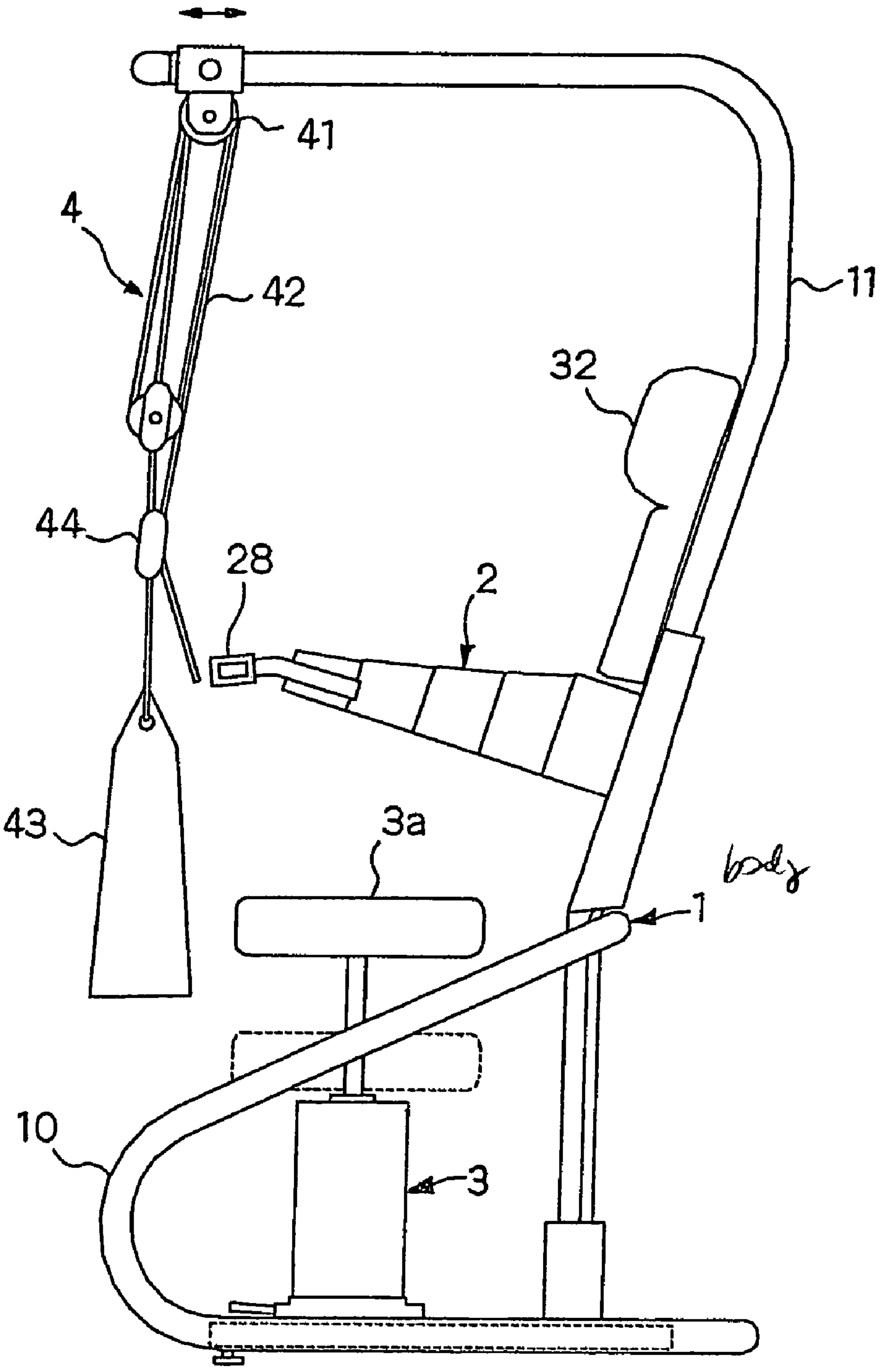
FIG. 2 is a side view of health equipment according to the first embodiment of the present invention.

FIG. 1 is a front view of health equipment according to the first embodiment of the present invention. FIG. 2 is a side view of health equipment according to the first embodiment of the present invention.

Health equipment according to the first embodiment of the present embodiment is an apparatus for supporting the trunk of the human and dragging the lumber by the weight of the lower part of the body. Health equipment comprises, as shown in FIG. 1 and FIG. 2, an equipment body 1, a trunk support 2 (trunk supporting means), a chair 3, and a leg hanging unit 4 (leg hanging means).

The equipment body 1 comprises a base frame 10 and a post 11 (supporting body) extended from the base frame 10 upwardly, and the post 11 extends behind the chair 3 and the upper portion thereof curves toward the front.

The trunk support 2 is a bendable member that holds and supports the trunk of the human. The trunk support 2 can be bended inwardly (toward the seated user), and wound around the trunk of the user, especially the area below the costae and above the pelvis. The trunk support 2 mainly comprises, as shown in FIG. 3 to FIG. 6, a trunk supporting arm 2A consisting of a plurality of supporting members 20 linked by the linking member 21, a pinching resistant member 22, a human body protecting member 23, 24, a resilient member 25, a covering member 26, a non-slip member 27, and a fastening belt 28.

Figure 4:
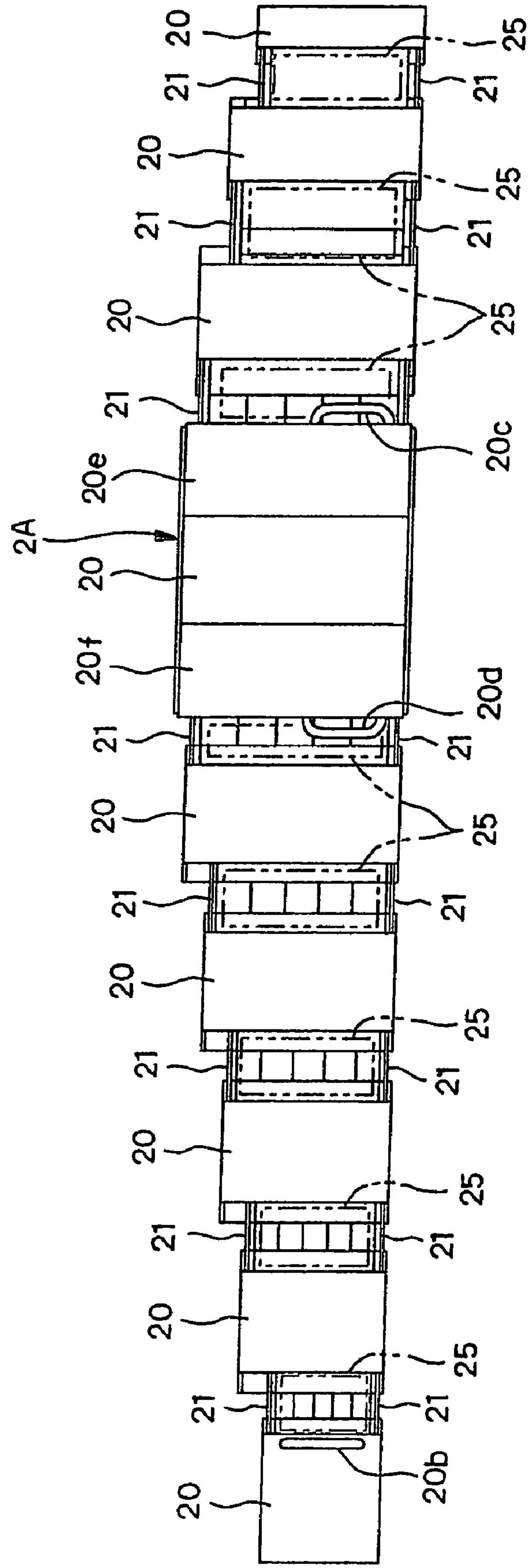
FIG. 4 is a rear elevation showing the trunk support of health equipment according to the first embodiment of the present invention.
Figure 5:
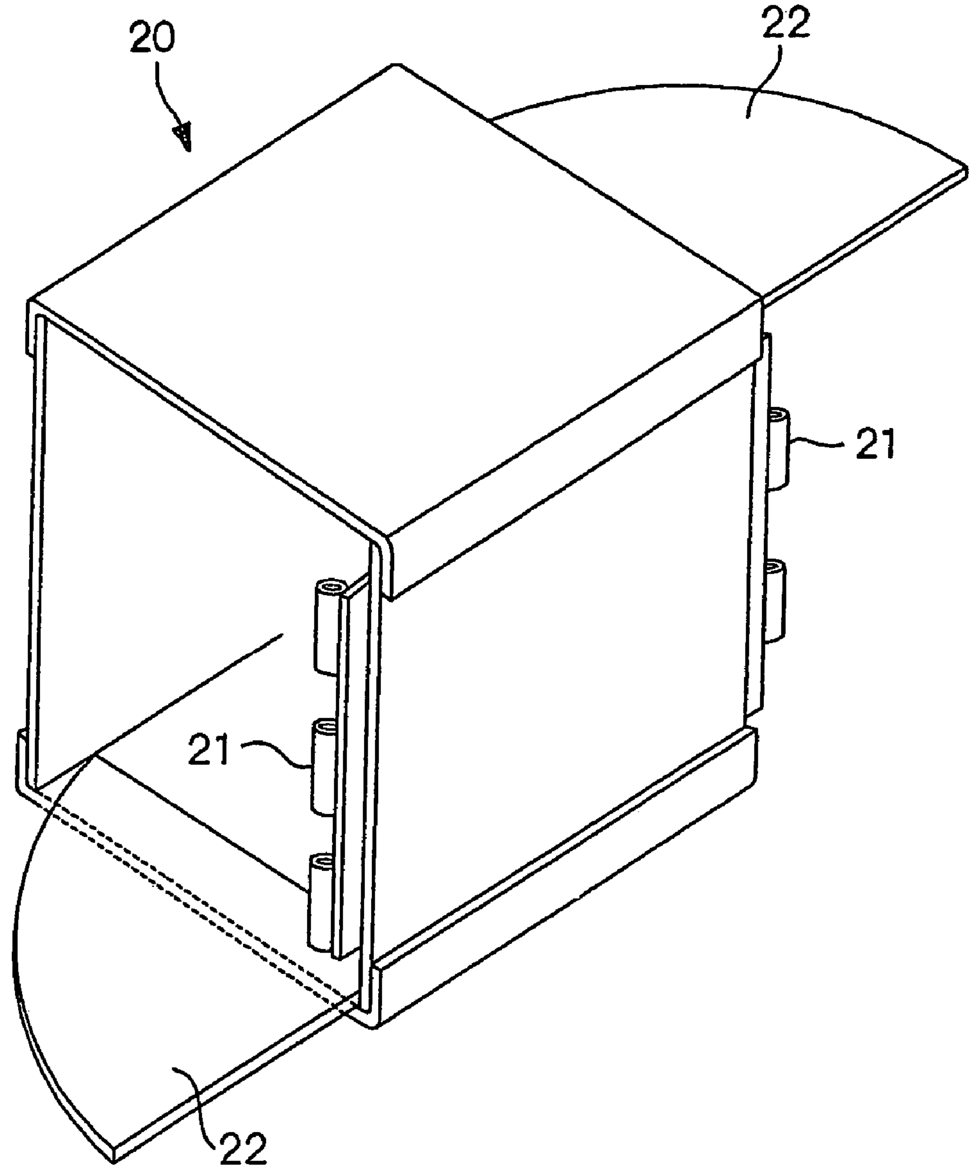
FIG. 5 is a perspective view of the supporting member of health equipment according to the first embodiment of the present invention.

As shown in FIG. 5, the supporting member 20 is a box-shaped frame opening on both sides and formed by bending and welding metal plates. The heights of the respective supporting members 20 are defined so as to be decreased in stages from the supporting member 20 in the midsection toward the supporting members 20 of both ends, as shown in FIG. 4. Especially in this embodiment, as shown in FIG. 4, the heights of the respective supporting members 20 are defined so that the height of the upper surface of the trunk supporting arm 2A is reduced in stages toward the ends.

Figure 3:
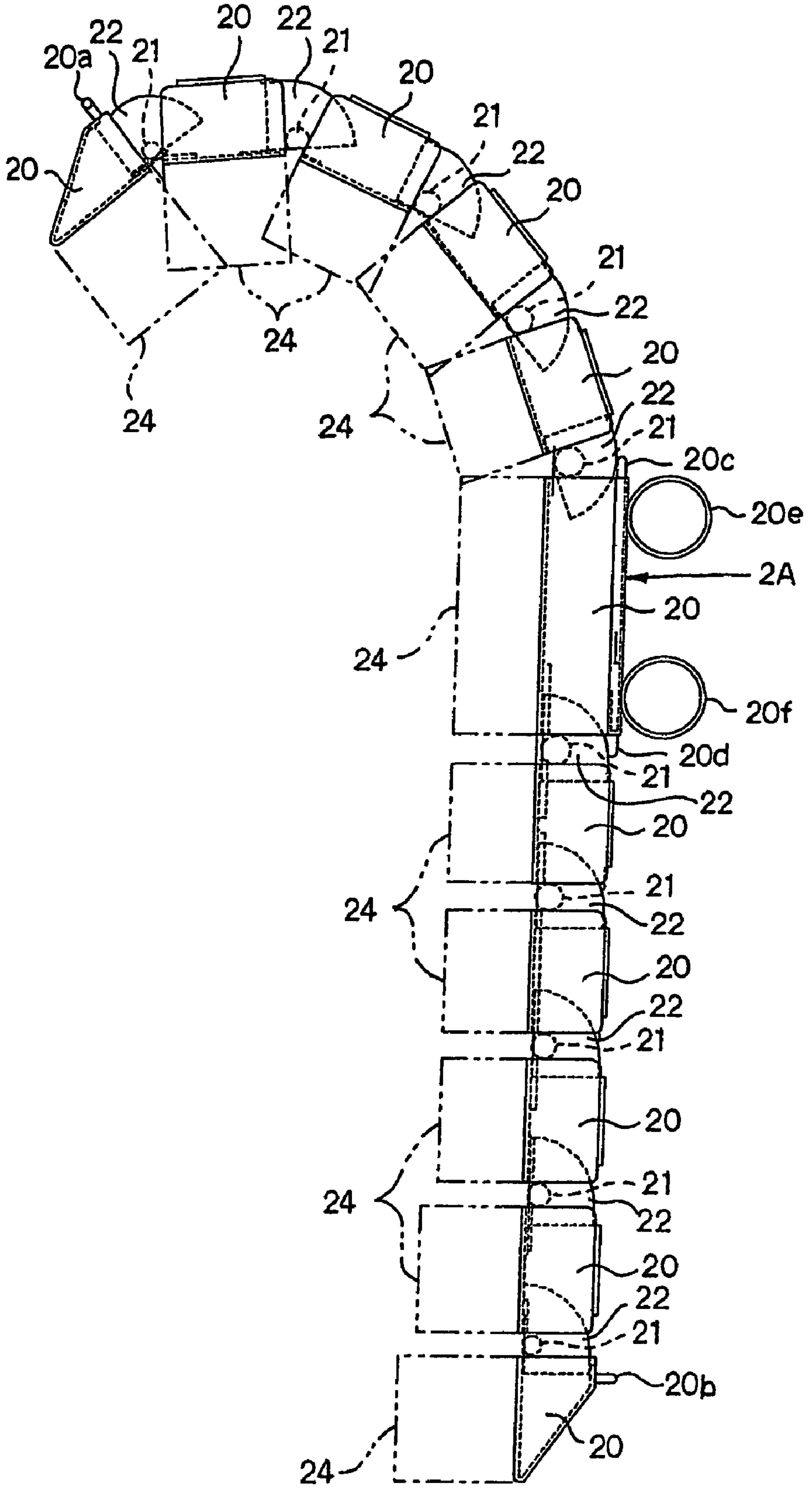
FIG. 3 is a plan view showing the trunk support of health equipment according to the first embodiment of the present invention.

As shown in FIG. 3, the supporting members 20 that are located near the ends are provided with belt guide rings 20_a_, 20_b_ welded thereto, and the supporting member 20 in the midsection is provided with belt fixing ring 20_c_, 20_d_ and mounting tubes 20_e_, 20_f_ welded thereto.

The supporting member 20 is fixed at the desired level by fitting the mounting tubes 20_e_, 20_f_ onto the post 11 and fixing by fixtures, not shown.

The linking member 21 is consisted of the hinge that links rotatably adjacent supporting members 20 each other. Any linking members 21 have approximately same structure. As shown in FIG. 5, the linking member 21 is welded with the adjacent supporting members 20 at the both side.

Since the linking members 21 are welded to the inner edges of the respective supporting members 20, the respective supporting members 20 are able to be turned inwardly, but not outwardly because the respective supporting members 20 interfere with respect to each other.

The pinching resistant member 22 is provided for preventing the human body from being pinched between the adjacent supporting members 20. The pinching resistant member 22 is, as shown in FIG. 3, formed of an approximately sector shaped metal plate so that it covers each rotating area of the supporting members 20 when linked with respect to each other. As shown in FIG. 5, each supporting member 20 is provided with the pinching resistant members 22 welded on the upper and lower sides located diagonally with respect to each other.

Figure 6:
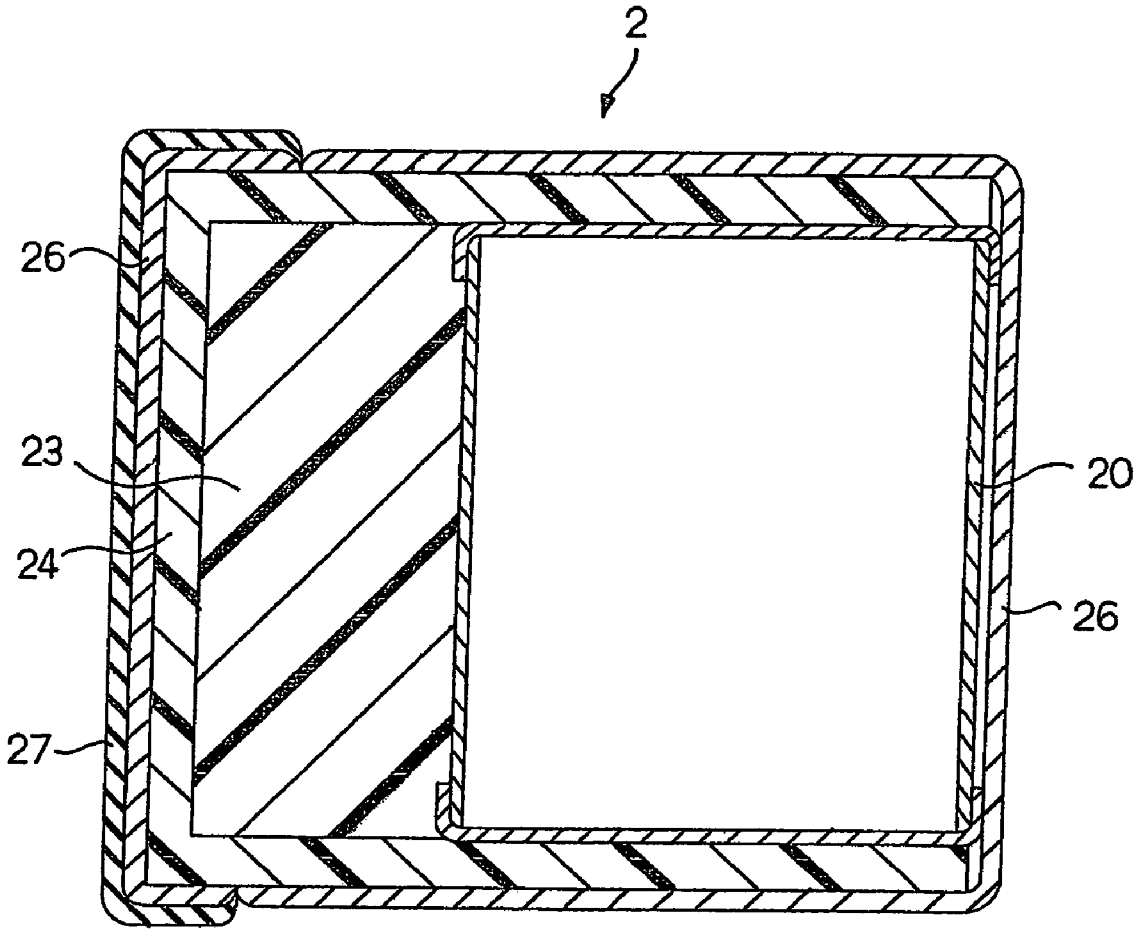
FIG. 6 is a cross sectional view showing the trunk support of health equipment according to the first embodiment of the present invention.

The human body protecting member 23, 24 is an resilient member for enfolding the trunk of the human softly and formed of a pliant resin material such as urethane resin. The human body protecting member 23 is, as shown in FIG. 6, attached on the inner side of the supporting member 20 and formed of a somewhat hard resin material to prevent it from losing its original shape.

The human body protecting member 24 is applied from the upper surfaces of the supporting member 20 and the human body protecting member 23 through the front face of the human body protecting member to the lower surfaces of the supporting member 20 and the human body protecting member 23. The human body protecting member 24 is formed of a resin member that is more pliant than that of the human body protecting member 23.

As shown in FIG. 3, the thickness of the human body protecting member 23 increases in stages from the supporting member 20 in the midsection toward the supporting member on the ends.

As shown in FIG. 4 with a phantom line, resilient members 25 formed of urethane resin or the like is inserted into the gaps formed on the back side between the adjacent supporting members 20. The resilient member 25 prevents the covering member 26 or the like described later from being pinched between the gaps on the back side described above. In addition, the resilient member 25 urges the supporting member 20 so as to turn inwardly, whereby each supporting member 20 is kept in an angled position with respect to the adjacent supporting member 20 to some extent.

The covering member 26 is made of antibacterial treated vinyl leather having alcohol resistant and benzine resistant properties. The covering member 26 covers whole part of the supporting member 20 and the human body protecting member 24 as shown in FIG. 6, provided that the mounting tubes 20*e* and 20*f* are exposed from the covering member 26.

The covering member 26 is seamed on the upper surface and lower surface of the trunk support 2 but not on the corner (specially the upper end corner).

The non-slip member 27 is a member that increases the contact resistance with respect to the trunk of the human to prevent slippage from occurring between itself and the trunk of the human, and thus formed of a embossed rubber sheet or the like. The non-slip member 27 is adhered to the inner surface of the covering member 26 and seamed together with the covering member 26 on the upper surface and the lower surface of the trunk support 2.

The fastening belt 28 is used for fastening the trunk support 2 around the trunk of the human. One end of the fastening belt 28 is fixed to the fixing rings 20*c* and 20*d* shown in FIG. 3 and FIG. 4, and the other end is exposed from the end portion of the covering member 26 through the guide rings 20*a*, 20*b* as shown in FIG. 2.

The chair 3 is arranged in the center portion of the base frame 10 as shown in FIG. 1 and FIG. 2. The chair 3 is constructed in such a manner that the seat portion 3*a* is movable in the vertical direction by means of hydraulic or pneumatic pressure and can be locked at desired levels, and the raising and lowering operation is done by an operating foot pedal 30 or an operating lever 31. The chair 3 having such raising and lowering function is known in the related art and thus the detailed description about the construction is omitted. However, the fact that the operating foot pedal 30 and the operating lever 31 are provided so that the user can raise or lower the seat by his or her foot or hand is novel construction of this embodiment.

The post 11 is provided with the seat back 32 right above the trunk support 2. The upright portion of the post 11 is inclined with respect to a vertical line to some extent, and the seat back 32 is also inclined correspondingly backwardly. Accordingly, the user's upper body is oriented a little upwardly when he or she is reclined against the seat back.

The leg hanging unit 4 comprises a pulley 41 attached on the post 11, a hanger string 42 for looping over the pulley 41, a leg holder 43 attached to the hanger string 42 for supporting the leg, and the stopper 44 for fixing the vertical position of the leg holder 43.

The leg hanging unit 4 is used for carrying out combined lumbago treatment called mobilization, wherein the ankles or the knees of the user are supported by the leg holder 43 and raised by the hanger string in order to suspend the legs of the human in the air.

In other words, the lower end of the hanger string 42 can be raised and lowered freely by manipulating the hanger string 42. The leg holder 43 attached on the lower end of the hanger string 42 is raised by releasing the stopper and pulling the hanger string 42, and the leg holder 43 is lowered by the reversal movement of the hanger string 42.

The pulley 41 is detachably mounted on the post 11 so that the leg hanging unit 4 can be provided as an optional accessory. The pulley 41 is adjustable in the forward and backward directions with respect to the post 11, so that the leg hanging unit 4 may be located at a proper position depending on the length of the user's legs.

How to use health equipment according to the first embodiment of the present invention will now be described.

Figure 7:
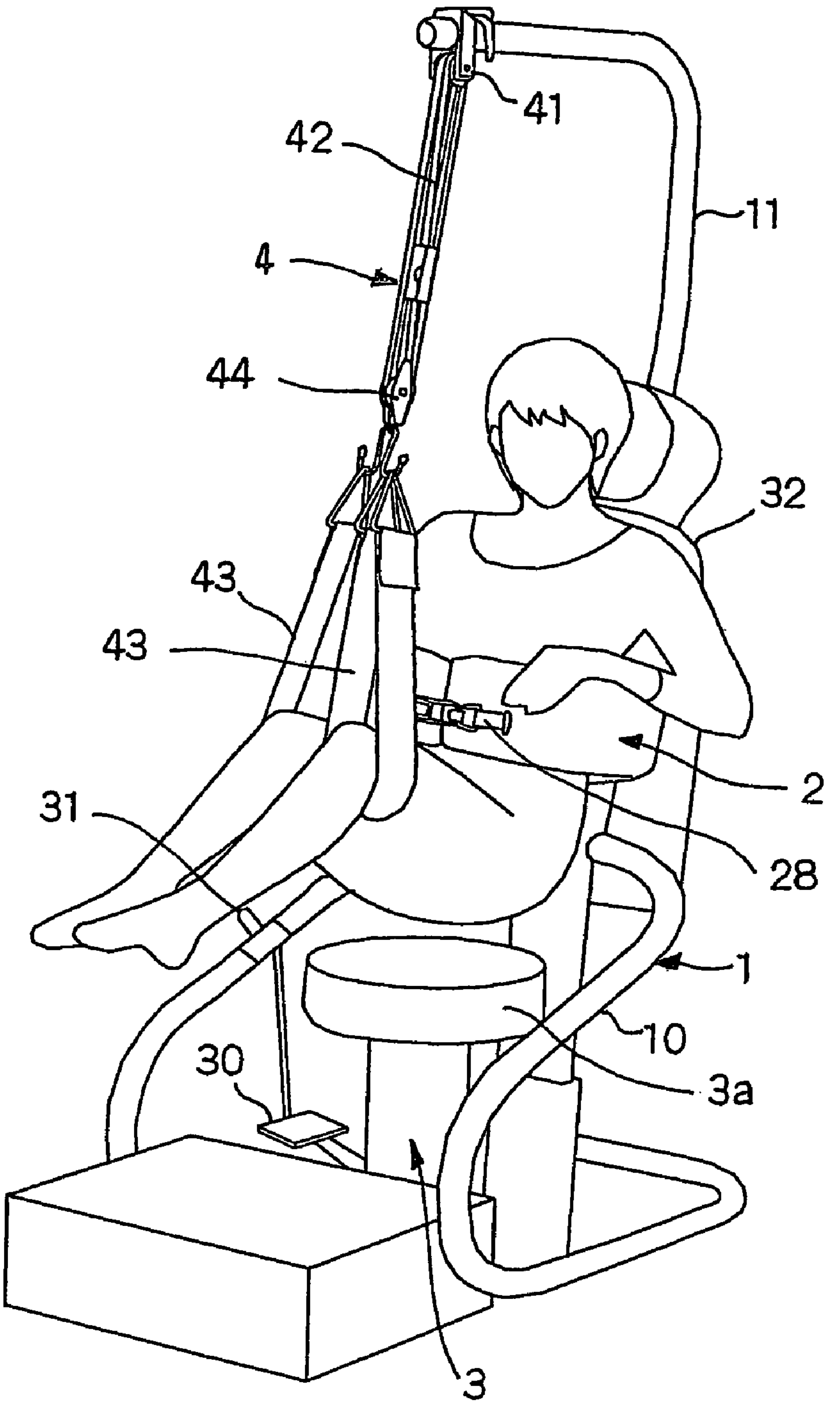
FIG. 7 is an explanatory drawing illustrating how to use health equipment according to the first embodiment of the present invention.

FIG. 7 is an explanatory drawing illustrating how to use health equipment according to the first embodiment of the present invention. Here, the method of performing combined lumbago treatment called mobilization will be described.

The chair 3 is positioned so that the seat portion 3*a* comes to the uppermost level. The trunk support 2 is fixed to almost the same level as the trunk of the human when he or she sits on the seat portion 3*a* at the uppermost level. The leg holder 43 is lowered in advance so that the user can easily attach the same 43 to his or her knees or ankles in the state where he or she is sitting on the seat portion 3*a*.

The user sits on the seat portion 3*a* and attaches the leg holder 43 on his or her knees or legs, and then he or she pulls the trunk support 2 inward to place it around his or her trunk and fastens the belt 28. By fastening the belt 28, the trunk support 2 is maintained in the state of holding the trunk of the human.

When the user operates the operating lever 31 to lower the seat portion 3*a*, the trunk of the human is supported by the trunk support 2 and the lower part of the body acts on the lumber, so that the lumber is dragged. In this case, it is preferable to lower the chair 3 until it comes out of contact with the hip with the aid of an assistant to ensure that the weight of the lower part of the body acts on the lumber.

In order to carry out mobilization, the stopper 44 is released and the hanger string 42 is pulled to raise the leg holder 43 to the desired level. According to the experiment of the present inventors, the most suitable posture of the user for mobilization was such that the trunk and the knees, and the knees and the shanks form an angle of approximately 90° respectively. However, since maintaining the same posture for a long time makes the user tired, it is preferable to change the level of leg holder 43 or the part to be supported by the leg holder 43 (for example from the knees to the ankles) in order to continue comfortable lumbago treatment.

Mobilization is an operation to turn the legs of the human left and right with the legs of the human hanged, as described above, in which a force in the twisting direction is applied to the lumber that is being dragged by the weight of the lower part of the body, thereby increasing the effectiveness of lumbago treatment.

In order to terminate lumbago treatment, the operation lever 31 is operated to raise the seat portion 3*a* of the chair 3 to the level where it comes into contact with the hip. Then the leg holder 43 is lowered to lower the legs to the floor and the fastened belt 28 is released to open the trunk support away from the trunk of the body.

Health equipment according to the first embodiment of the present invention described above has effects as follows.

(a) In the first embodiment of the present invention, since the trunk of the body is supported by the trunk support 2 and the lumbar is dragged by the weight of the lower part of the body of the patient, there is no possibility to drag the lumber with an excessive load and it is not necessary to use electricity, whereby safeties during use is ensured.

(b) In the first embodiment of the present invention, since the trunk support 2 is constructed to be bendable by linking the adjacent members 20 rotatably by the linking member 21, the trunk of the human can be enfolded and supported almost uniformly independently of the figure of the trunk of the human or the size of the waist. Therefore, the human body can be supported reliably.

(c) In the first embodiment of the present invention, the space for installation may be decreased in comparison with the conventional bed for lumbago treatment to make full use of the space for treatment, for example, in the hospital.

(d) In the first embodiment of the present invention, since the heights of the supporting members 20 decrease in stages from the midsection toward the end portions which support the belly of the human body, the feeling that the trunk support 2 is fitted to the trunk of the body is improved, thereby decreasing the feeling of being in contact with a foreign substance, or the feeling of being pressed on his or her belly. Therefore, lumbago treatment can be continued without giving any suffering to the user.

(e) In the first embodiment of the present invention, since the pinching resistant member 22 is provided on the upper side and the lower side of the supporting member 20, a part of the body, the human body protecting member 24, or the covering member 26 may be prevented from being pinched in the gaps between the adjacent supporting members 20.

(f) In the first embodiment of the present invention, the human body protecting member 23 is attached on the inner side of the supporting member 20. Therefore, the trunk support 2 can enfold the trunk of the body softly while providing a sufficient force for supporting the human body and the feeling of being in contact with the core or the feeling of being pressed may be resolved. In addition, even when the trunk of the body is tightly fastened with the trunk support 2 to some extent, the pressure applied to the belly is dispersed by the human body protecting member 23, thereby alleviating the feeling of being pressed.

(g) In the first embodiment of the present invention, since the human body protecting member 23 is thicker on the portion near the ends that support the belly of the body, the trunk support 2 may be fitted to the belly of the body corresponding to a depression of the belly due to a tight fastening.

(h) In the first embodiment of the present invention, since a non-slip member 27 is provided on the inner surface of the covering member 26, contact resistance between the trunk support 2 and the trunk of the body is increased to prevent slippage, thereby supporting the human body securely.

(i) In the first embodiment of the present invention, since the non-slip member 27 and the covering member 26 are seamed at the portion other than the corner of the trunk support 2, there is little possibility to give the user the feeling of being in contact with a foreign substance that the user may have upon contact with the seamed portion.

(j) In the first embodiment of the present invention, so called mobilization may be carried out with the legs of the patient hanged by the leg hanging unit 4 and the lower portion of the back suspended away from the chair 3, whereby the effectiveness of lumbago treatment may be increased.

Only by support the trunk of the body with the trunk support 2 to keep the hip being suspended away from the chair 3 without using the leg hanging unit 4, the weight of the lower part of the body acts on the lumber to some extent and the lumber is dragged to enjoy the effectiveness of lumbago treatment.

Second Embodiment

Figure 8:
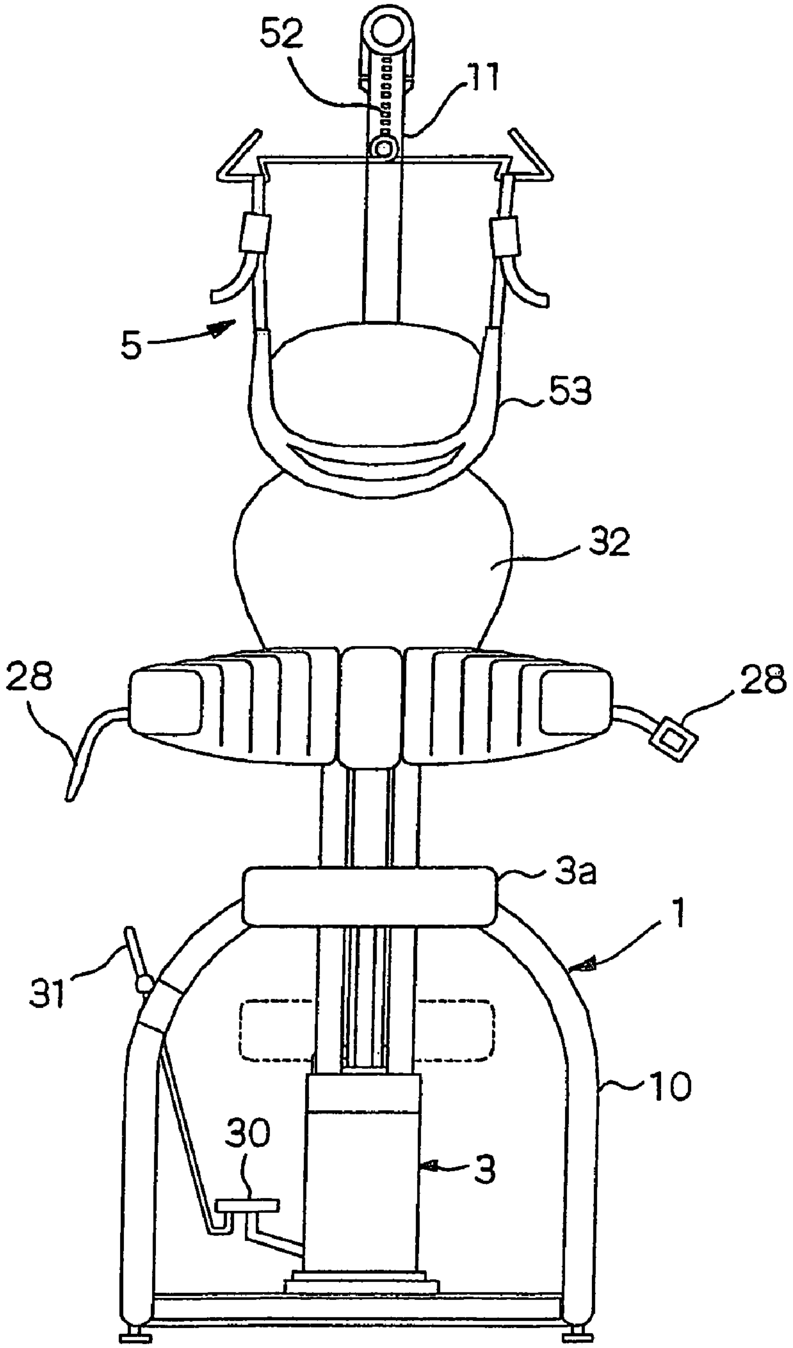
FIG. 8 is a front view of health equipment according to the second embodiment of the present invention.
Figure 9:
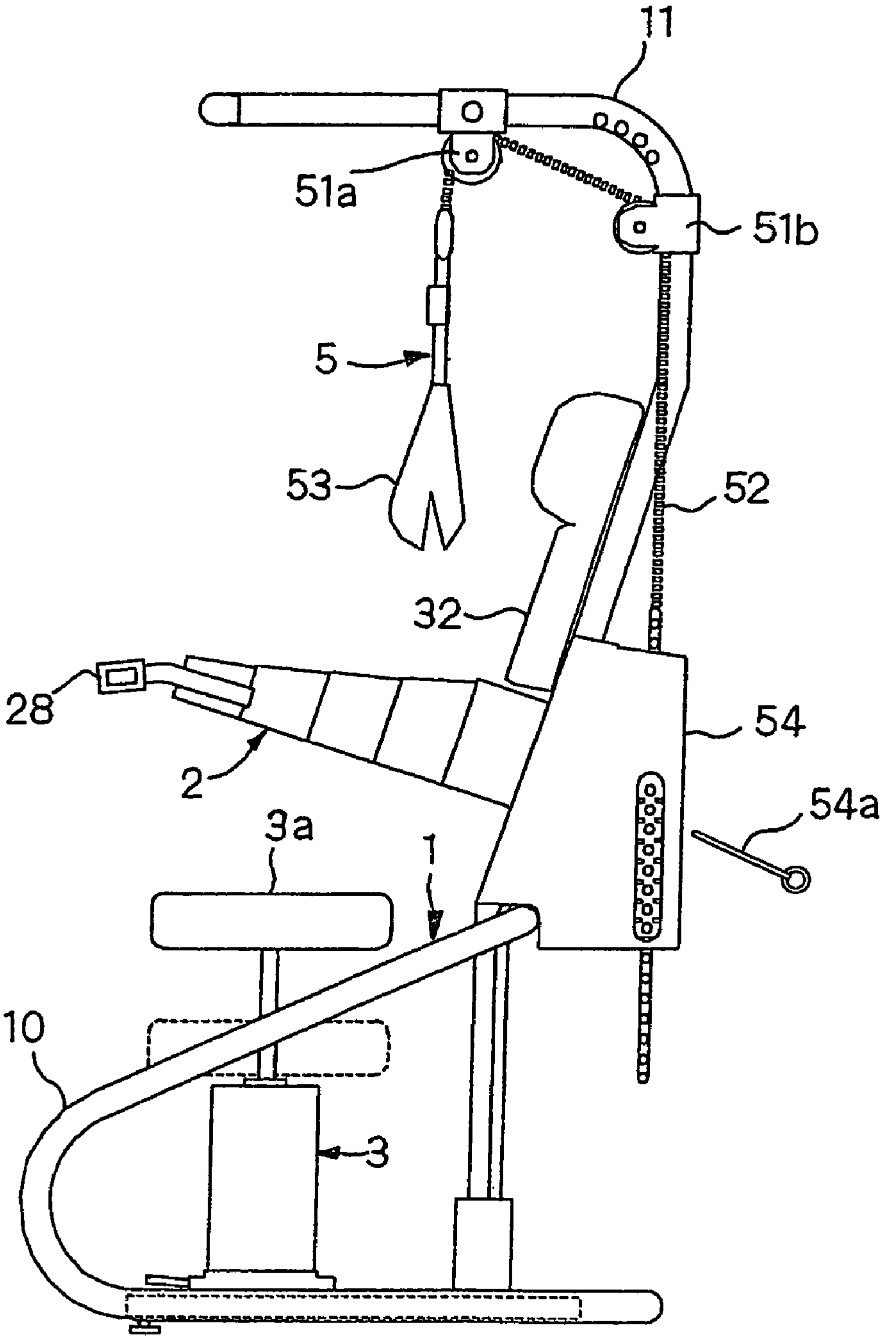
FIG. 9 is a side view of health equipment according to the second embodiment of the present invention.

FIG. 8 is a plan view of health equipment according to the second embodiment of the present invention. FIG. 9 is a side view of health equipment according to the second embodiment of the present invention. The identical numerals are designated to the members identical to those shown in FIG. 1 to FIG. 7, and the detailed description thereof is omitted.

In the second embodiment of the present invention, a chin holding unit 5 (cervical vertebrae dragging means) is mounted on the post 11 (supporting body) instead of the leg hanging unit 4 of the first embodiment.

The chin holding unit 5 is used for dragging the cervical vertebrae with the chin of the human supported, and is effective for treating whiplash injury, stiff shoulder or the like. The chin holding unit 5 may be provided as a optional accessory as in the case of the leg hanging unit 4.

The chin holding unit 5 comprises pulleys 51*a*, 51*b* detachably mounted to the post 11, a wire 52 looped over these pulleys 51*a*, 51*b*, a chin holder 53 attached on the end of the wire 52 for placing under the chin of the human body, and a load adjuster 54 for adjusting the load applied to the chin holder 53 by changing the position of insertion of a pin 54*a*. The load adjuster 54 is fixed on the post 11 by the fixture such as a bolt or the like.

How to use health equipment according to the second embodiment of the present invention will now be described.

The user adjusts a load applied to the chin holder 53 by the load adjuster 54 and sits on the seat potion 3*a* of the chair 3, and then places the chin holder 53 under his or her chin. Then, a load from the load adjuster 54 is transmitted to the chin holder 53 via the wire 52 so that the cervical vertebrae of the user may be dragged.

When carrying out dragging treatment for the cervical vertebrae by the use of the chin holding unit 5, the use of the trunk support 2 described above is not essential. However, by combining with the trunk support 2, the chin is dragged with the trunk of the body supported, whereby only the bones of the upper part of the body are dragged, and thus improvement of the effectiveness of treatment can be expected.

Third Embodiment

Figure 10:
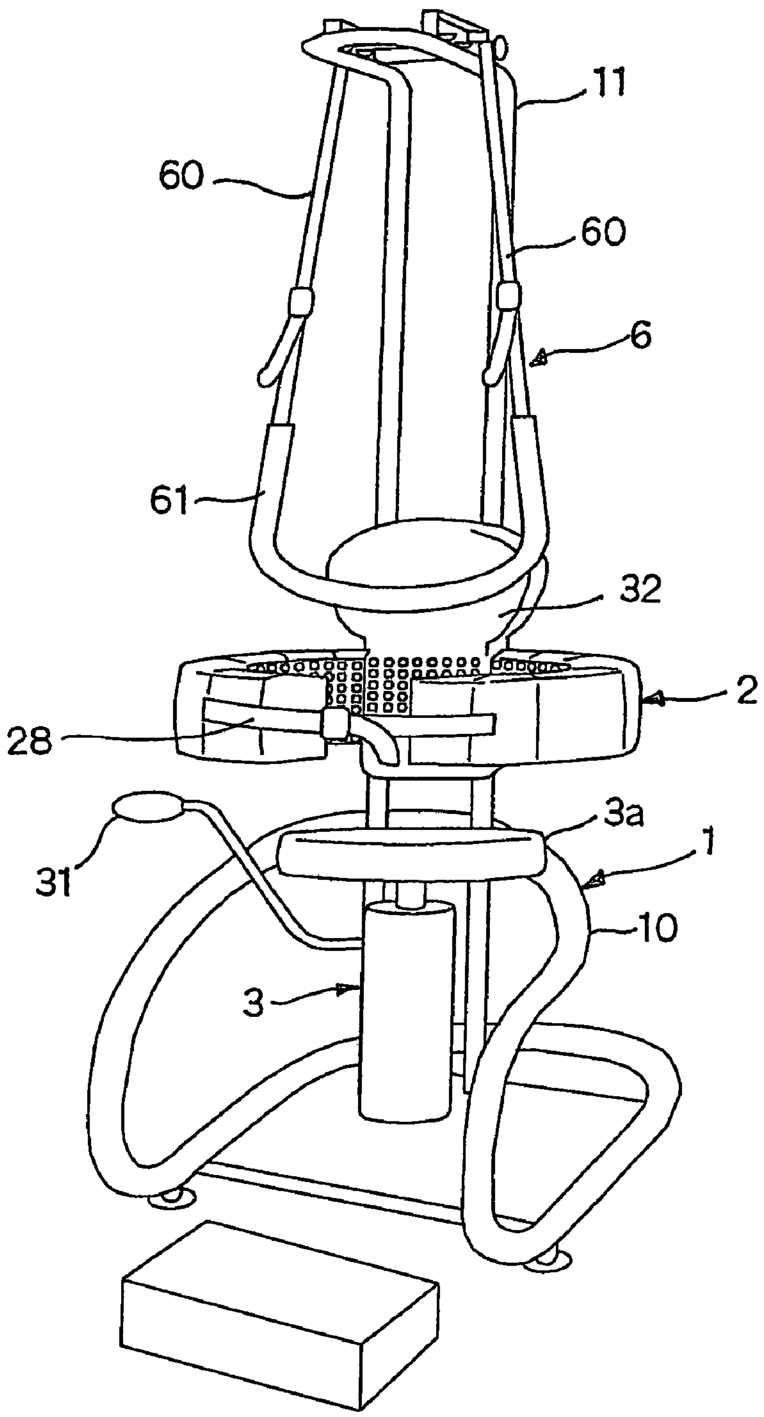
FIG. 10 is a perspective view of health equipment according to the third embodiment of the present invention.
Figure 11A:
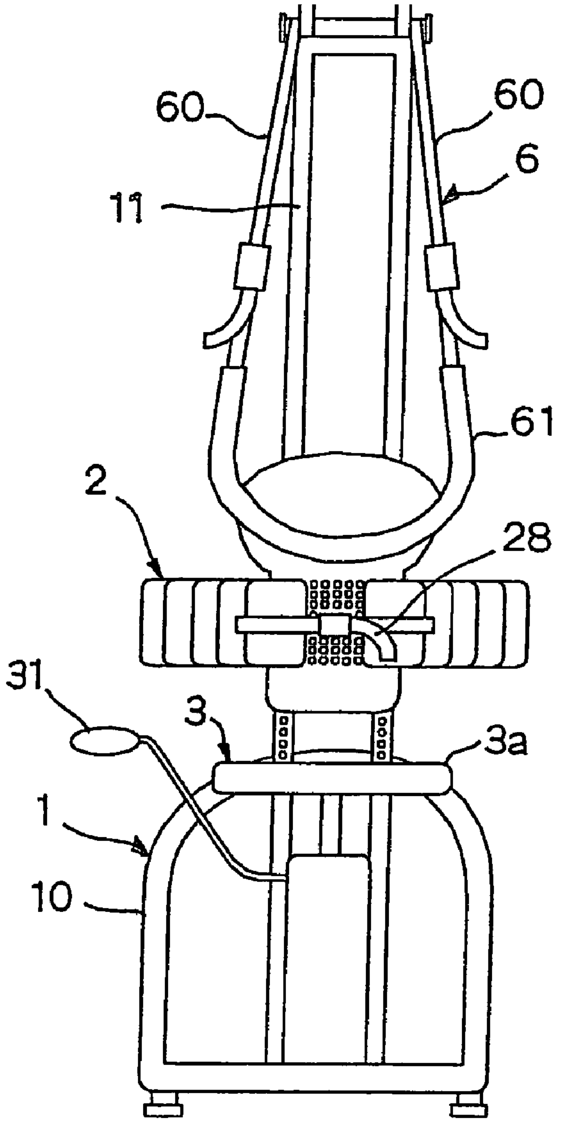
FIG. 11A is a front view of health equipment according to the third embodiment of the present invention.
Figure 11B:
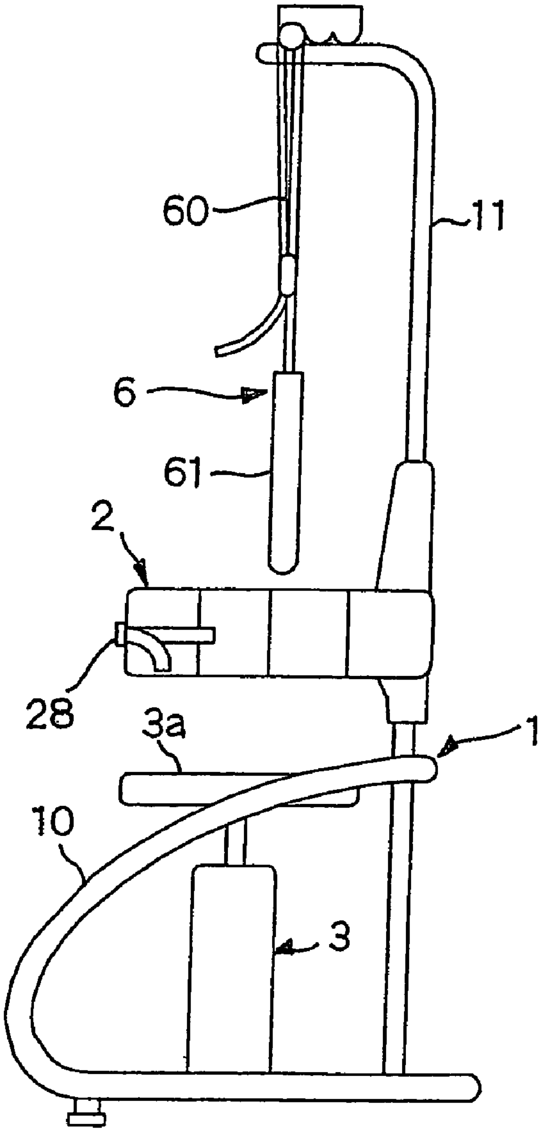
FIG. 11B is a side view of health equipment according to the third embodiment of the present invention.

FIG. 10 is a perspective view of health equipment according to the third embodiment of the present invention. FIG. 11A is a plan view of the same health equipment, FIG. 11B is a side view of the same health equipment. Hereinafter, the identical reference numerals are designated to the identical or corresponding members as those in FIG. 1 to FIG. 7, and the detail description is omitted.

Health equipment according to the third embodiment of the present invention, a shoulder hanging unit 6 (shoulder hanging means) is provided instead of the leg hanging unit 4 of the first embodiment. The shoulder hanging unit 6 comprises a belt portion 60 hanged from the post 11 (supporting body), and a shoulder attachment 61 formed at the lower portion of the belt portion 60, wherein the belt portion 60 is constructed in such a manner that the length thereof can be adjusted. The shoulder attachment 61 is provided with a cushion member wound thereon for alleviating the feeling of being in contact with the foreign material and suffering during dragging operation when it is attached to underarms of the human body.

In this embodiment, the configuration of the post 11 (supporting body) is modified since it supports both end of the shoulder hanging unit 6 at a certain distance (for example, a distance corresponding to the breadth of the user's shoulder). Though the trunk support 2 is formed at a regular level along it length, a construction shown in the first embodiment shown above may be employed as well.

Figure 12:
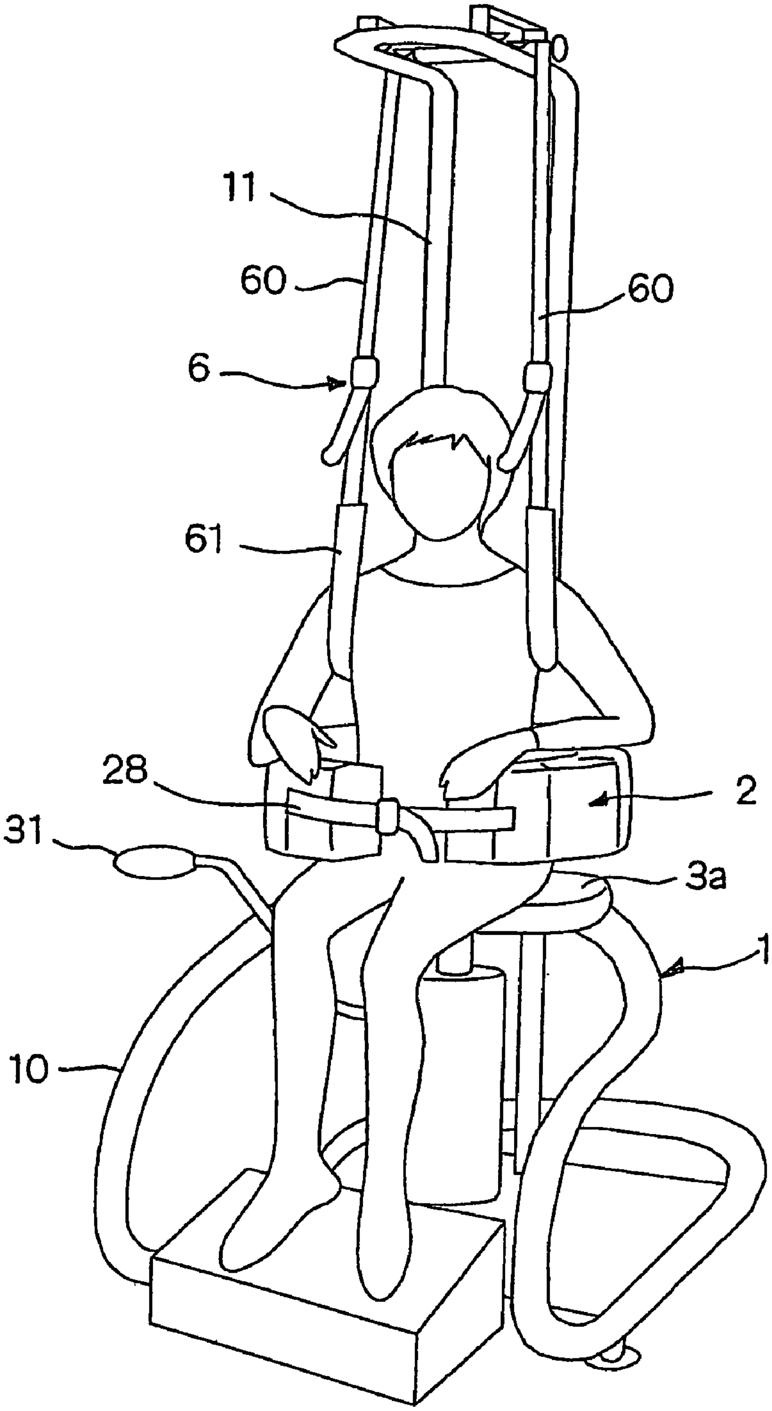
FIG. 12 is an explanatory drawing illustrating how to use health equipment according to the third embodiment of the present invention.

Referring now to FIG. 12, how to use health equipment according to the third embodiment of the present invention will be described.

The user attaches the trunk support 2 around the trunk of the body in the state of being seated on the seat portion 3*a* of the chair 3, and attaches the shoulder attachment 61 of the shoulder hanging unit 6 on underarms of the body. Then he or she lowers the chair 3 and creates the state where the lower part of his or her body is suspended in the air, whereby the lumber is dragged by the weight of the lower part of the body as in the case of the first embodiment.

According to health equipment of the third embodiment, since the trunk of the user is supported by the trunk support 2 and the upper part of the body is hanged by the shoulder hanging unit 6, the human body can be prevented reliably from being slipped down.

In addition, since the shoulder of the body is dragged upwardly by the shoulder hanging unit 6, the shoulder pain in the dragging type or compression type, which is one of symptoms of thoracic outlet syndrome, may be alleviated.

This shoulder hanging unit 6 may be provided as an optional accessory.

Fourth Embodiment

Figure 13A:
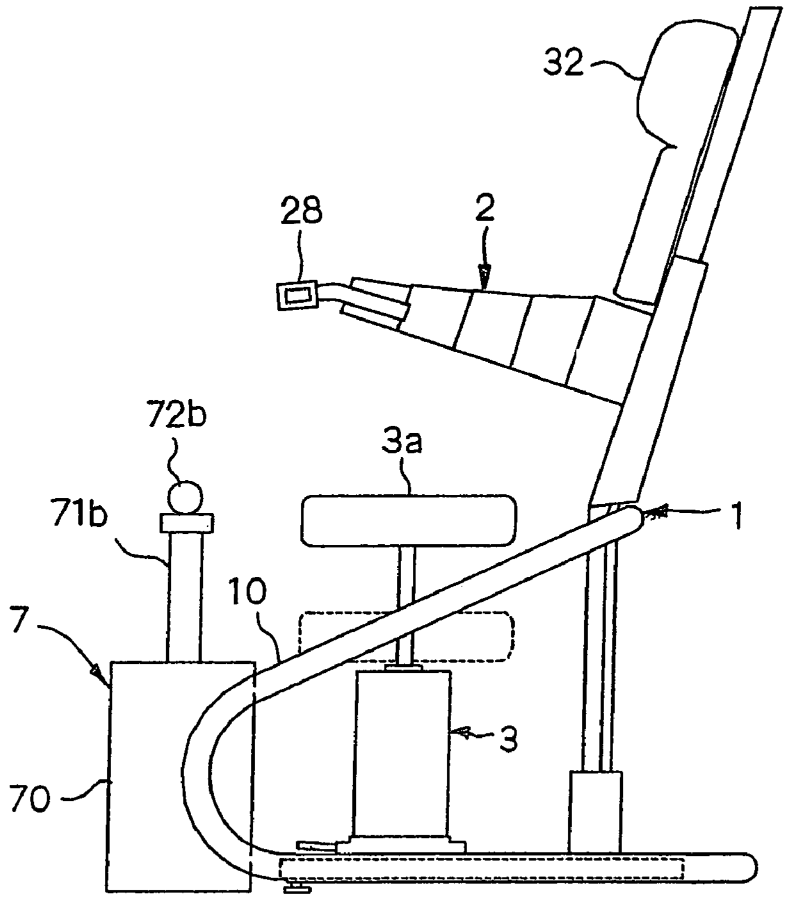
FIG. 13A is a side view of health equipment according to the fourth embodiment of the present invention.

FIG. 13A is a side view of health equipment according to the fourth embodiment of the present invention. Hereinafter, the identical numerals are designated to the components identical to those shown in FIG. 1 to FIG. 7, and the detailed description will be omitted.

In the second embodiment of the present invention, a leg raising/lowering device 7 (leg exercising means) is arranged forward of the equipment body 1 instead of the leg hanging unit 4 of the first embodiment.

The leg raising/lowering device 7 is used for applying a moderate stimulation properly to the lumber by forcing the legs of the user to move in the upward and downward directions, thereby increasing effectiveness of lumbago treatment.

Figure 13B:
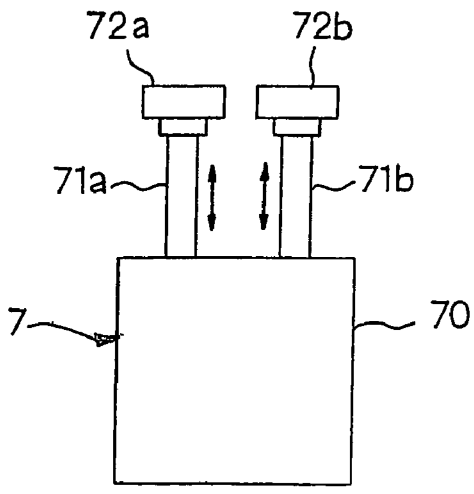
FIG. 13B is a front view of the leg raising/lowering device of health equipment according to the fourth embodiment of the present invention.

The leg raising/lowering device 7 is, as shown in FIG. 13B, constructed in such a manner that the leg supporting potions 72*a* and 72*b* are attached to the upper ends of a pair of drive shafts 71*a*, 71*b* mounted on the raising/lowering mechanism 70 respectively.

The raising/lowering mechanism 70 is able to drive the drive shafts 71*a*, 71*b* independently in the upward and downward directions. Independent driving of the drive shafts 71*a* and 7*b* can be realized for example by providing the drive sources (electric motor, hydraulic cylinder, etc.) independently, or by constructing in such a manner that the power is transmitted from the drive source via a clutch to the drive shafts 71*a*, 71*b*.

The leg supporting portions 72*a*, 72*b* are formed in the shape suitable to place the knees or legs of the body thereon (for example a cylindrical column). The leg supporting portion 72*a*, 72*b* may be formed of metal or of plastic pipe, or of a pliant resin.

The user pulls the trunk support 2 inward in the state of being seated on the seat portion 3*a* of the chair 3, and places it around his or her trunk, and then fasten the belt 28. By fastening the belt 28, the trunk support 2 is maintained in the state of holding the trunk of the human.

Then the user places his or her left and right knees or ankles on the leg supporting portions 72*a*, and 72*b* separately.

When the user operates the operating lever 31 to lower the seat portion 3*a*, the trunk of the human is supported by the trunk support 2 and the lower part of the body acts on the lumber, so that the lumber is dragged.

In addition, by raising and lowering the leg supporting portions 72*a*, 72*b* by actuating the raising/lowering mechanism, the legs moves upward and downward so that the lumber receives the moderate amount of stimulation. At this time, by driving the leg supporting portions 72*a*, 72*b* separately, the right leg and the left leg can do exercise independently. The leg raising/lowering device 7 may also be provided as an optional accessory.

Fifth Embodiment

Figure 14A:
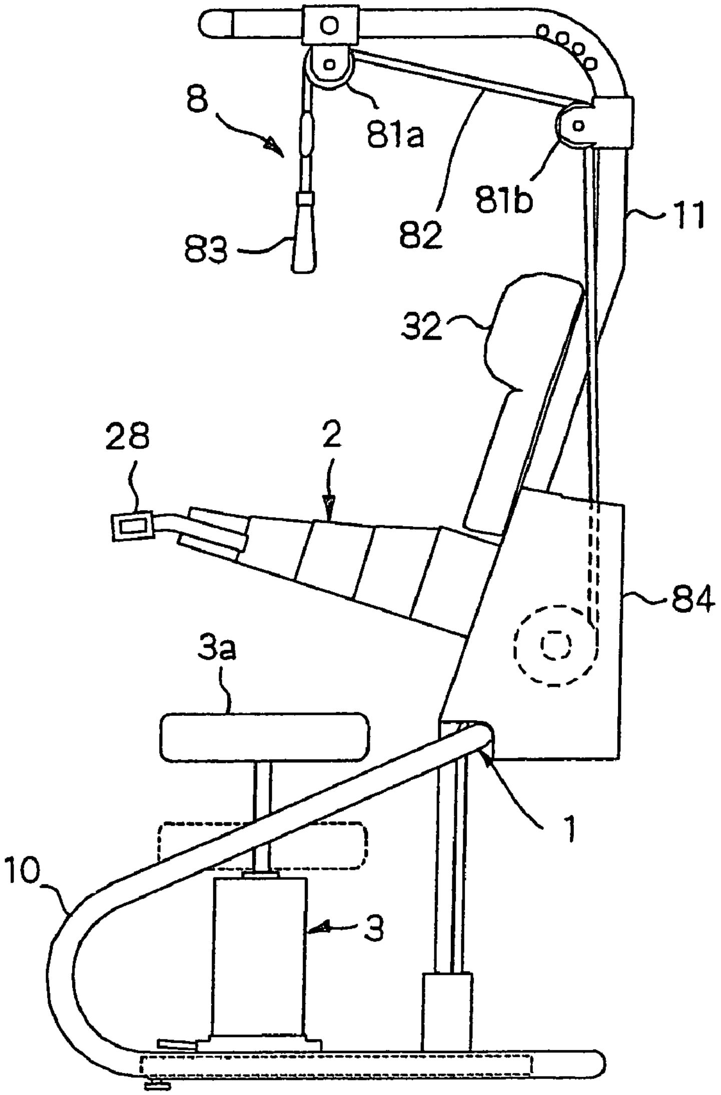
FIG. 14A is a side view of health equipment according to the fifth embodiment of the present invention.

FIG. 14A is a side view of health equipment according to the fifth embodiment of the present invention. Hereinafter, the identical reference numerals are designated to the identical or corresponding members as those in FIG. 1 to FIG. 7, and the detail description is omitted.

Health equipment according to the fifth embodiment of the present invention is provided with a load applied dragging unit 8 (rehabilitation means) mounted on the post 11 (supporting body) instead of the leg hanging unit 4 of the first embodiment. The load applied dragging unit 8 may be provided as an optional accessory, and is suitable to carry out rehabilitation of the arms or legs independently of the dragging of the lumber.

The load applying dragging unit 8 comprises pulleys 81*a*, 81*b* detachably mounted to the post 11 (supporting body), a wire 82 looped over these pulleys 81*a*, 81*b*, an operating portion 83 mounted to the end of the wire 82, and a resistor 84 mounted on the back side of the equipment body 1.

Figure 14B:
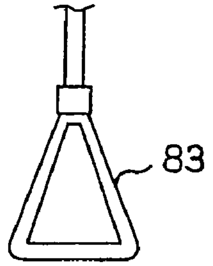
FIG. 14B is a front view showing the operating portion of health equipment according to the fifth embodiment of the present invention.

The operating portion 83 is formed in the handle shape that is convenient to grip as shown in FIG. 14B. In case where it is used for rehabilitation of the legs, it is preferable to form the operating portion 83 in the shape suitable to support the legs (for example the shape like the leg holder 43 of the first embodiment).

The position of the pulley 81*a* is adjustable in the forward and backward direction along the post 11, so that it comes to the convenient position depending on the length of the arms of the user.

The resistor 84 is used to apply a tensile strength to the wire 82, and may be used together with various kinds of known tensile strength applying mechanisms such as a mechanism using magnetic force of a permanent magnet, or a mechanism using a spring force of a helical spring. Preferably, the resistor 84 has a function to wind the wire 82 as well as a function to apply a tensile strength to the wire 82. The load adjustor 54 used in the second embodiment may be used as a resistor 84.

The user grips the operating portion 83 in the state of being seated on the seat portion 3*a* of the chair 3, and repeats exercise to pull the wire 82, which contributes to the recovery of the muscular strength. In addition, bending the body forward while gripping the operating portion 83 may contribute to the recovery of the muscular strength of the upper part of the body, and pulling down the wire 82 by the legs with the legs hanged on the operating portion 83 may contribute to the recovery of the muscular strength of the legs.

Sixth Embodiment

Figure 15:
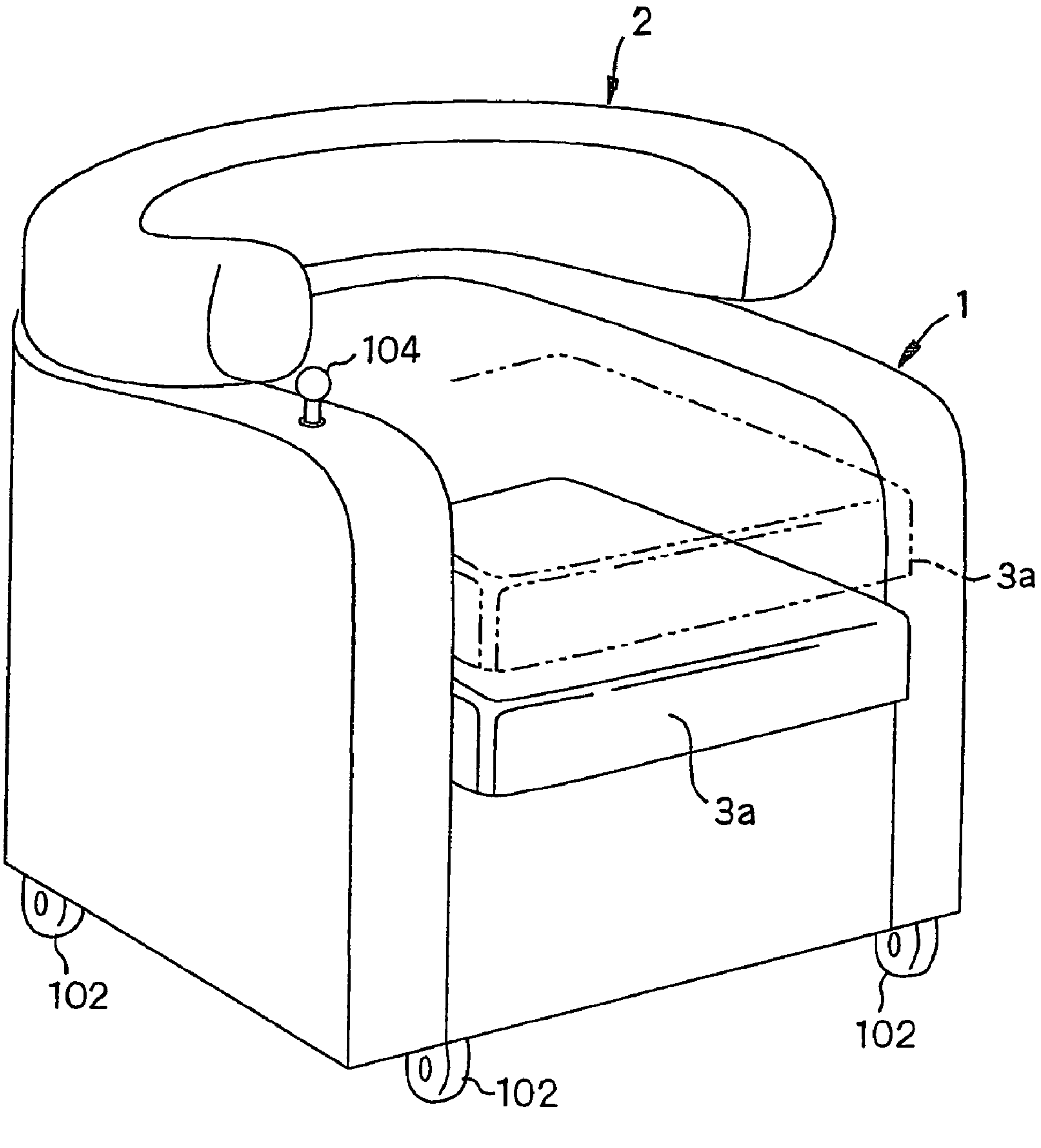
FIG. 15 is a perspective view of health equipment according to the sixth embodiment of the present invention.
Figure 16:
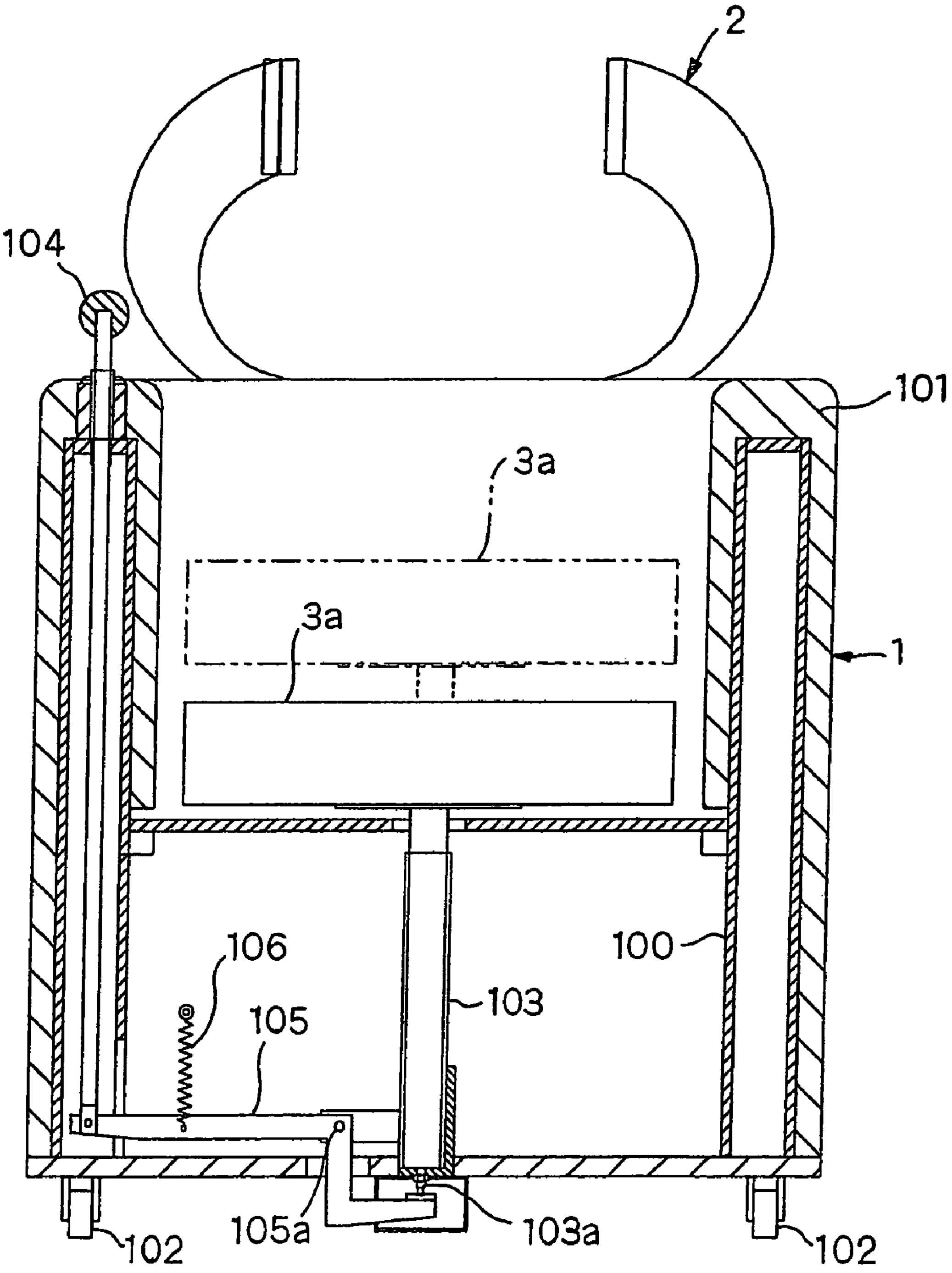
FIG. 16 is a front cross-sectional view of health equipment according to the sixth embodiment of the present invention.

FIG. 15 is a perspective view of health equipment according to the sixth embodiment of the present invention, and FIG. 16 is a cross sectional front view of the same. Hereinafter, the identical reference numerals are designated to the identical or corresponding members as those in FIG. 1 to FIG. 7, and the detail description is omitted.

In health equipment according to the sixth embodiment of the present invention, the equipment body is formed in the shape of an armchair, whereby it can be used as an armchair usually. As shown in FIG. 16, in the equipment body 1, there is provided a pliant cushion member 101 such as a urethane resin around the frame 100 formed by assembling wood material. It is preferable to cover the surface of the equipment body 1 with a material such as synthetic leather to give it an excellent looks, so that it can use in the living room for an ordinary households without giving the feeling of abnormality. By providing casters 102 on the bottom surface of the equipment body 1, it can be easily moved.

The trunk support 2 is mounted on the upper part of the back surface (seat back) of the equipment body 1. The structure of the trunk support 2 is the same as that explained in conjunction with the first embodiment referring to FIG. 3 to FIG. 6.

The seat portion 3*a* is arranged at the sitting position of the equipment body 1, and raised and lowered by the pneumatic raising/lowering device 103 provided within the equipment body 1. The raising/lowering device 103 is actuated by pressing operation of the operating lever 104 provided on the armrest of the equipment body 1. In other wards, by pressing the operating lever 104, the air purging portion 103*a* of the raising/lowering device 103 is pressed via a linkage 105 so that the raising/lowering device 103 becomes free to move upward and downward. The linkage 105 is urged clockwise in the figure about a fulcrum 105*a* by the spring member 106, and automatically moves toward the direction that releases pressure applied onto the air purging portion 103*a* by releasing pressure of the operating lever 104.

When the user places the trunk support 2 around the trunk of the body with the seat portion 3*a* raised, and lowers the seat portion 3*a* by pressing down the operating lever 104, the weight of the lower part of the body acts on the lumber with the trunk supported by the trunk support 2, whereby lumber treatment may be easily carried out.

Other Embodiments

Health equipment of the present invention is not limited to the embodiments described thus far, but various modifications or applications as follows may be made.

Figure 17:
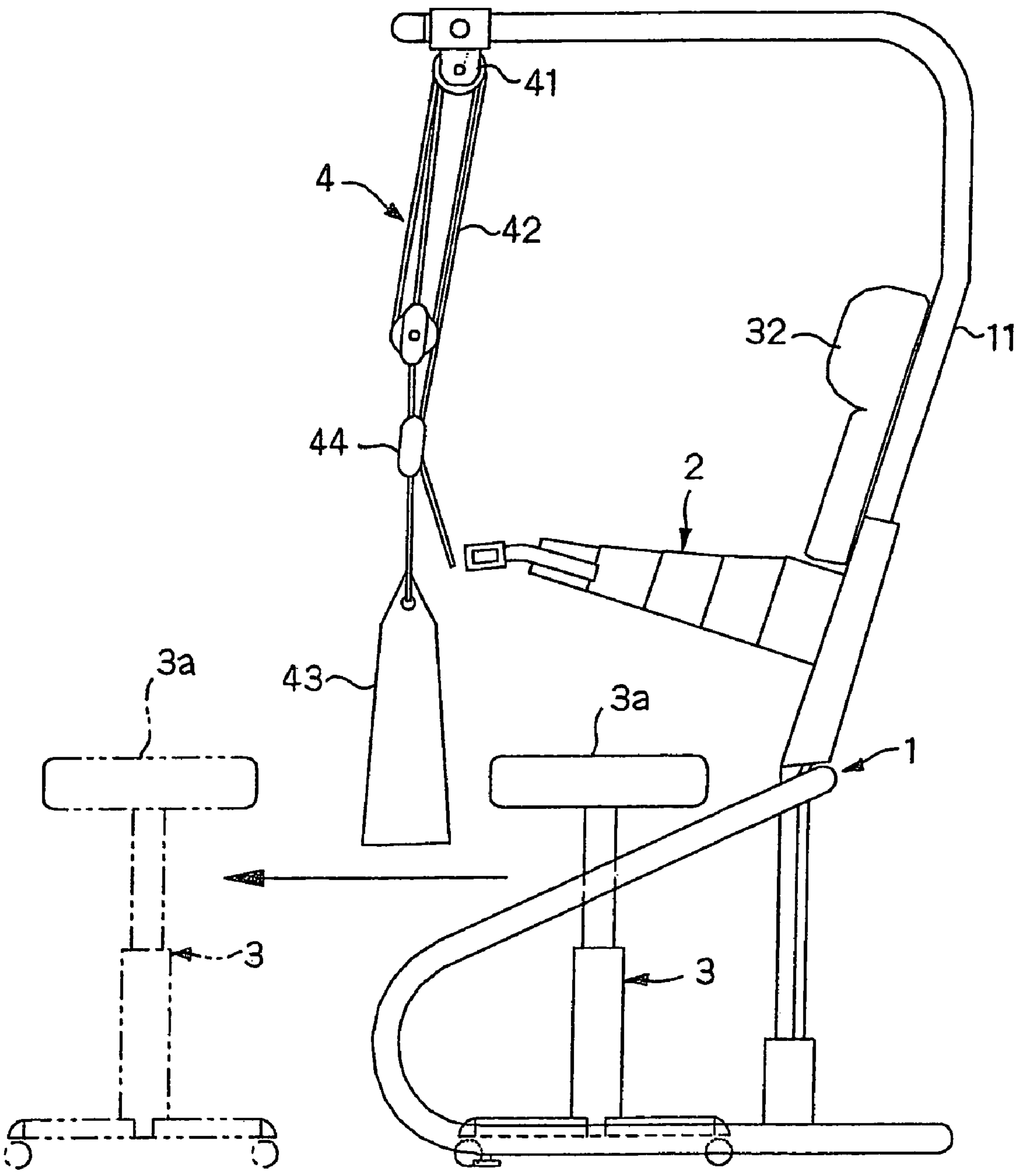
FIG. 17 is an explanatory side view illustrating health equipment according to another embodiment of the present invention.

(1) In the embodiments described thus far, the seat portion 3*a* can be moved upward and downward. However, it is also possible to employ the construction in which the chair 3 is easily removable from the position where the user is sitting as shown in FIG. 17, so that the seat portion 3*a* does not have to be movable upward and downward.

(2) By employing the structure in which the trunk support 2 moves up and down relative to the equipment body 1, the seat portion 3*a* does not have to be movable upward and downward and it is not necessary to remove the chair 3.

Figure 18:
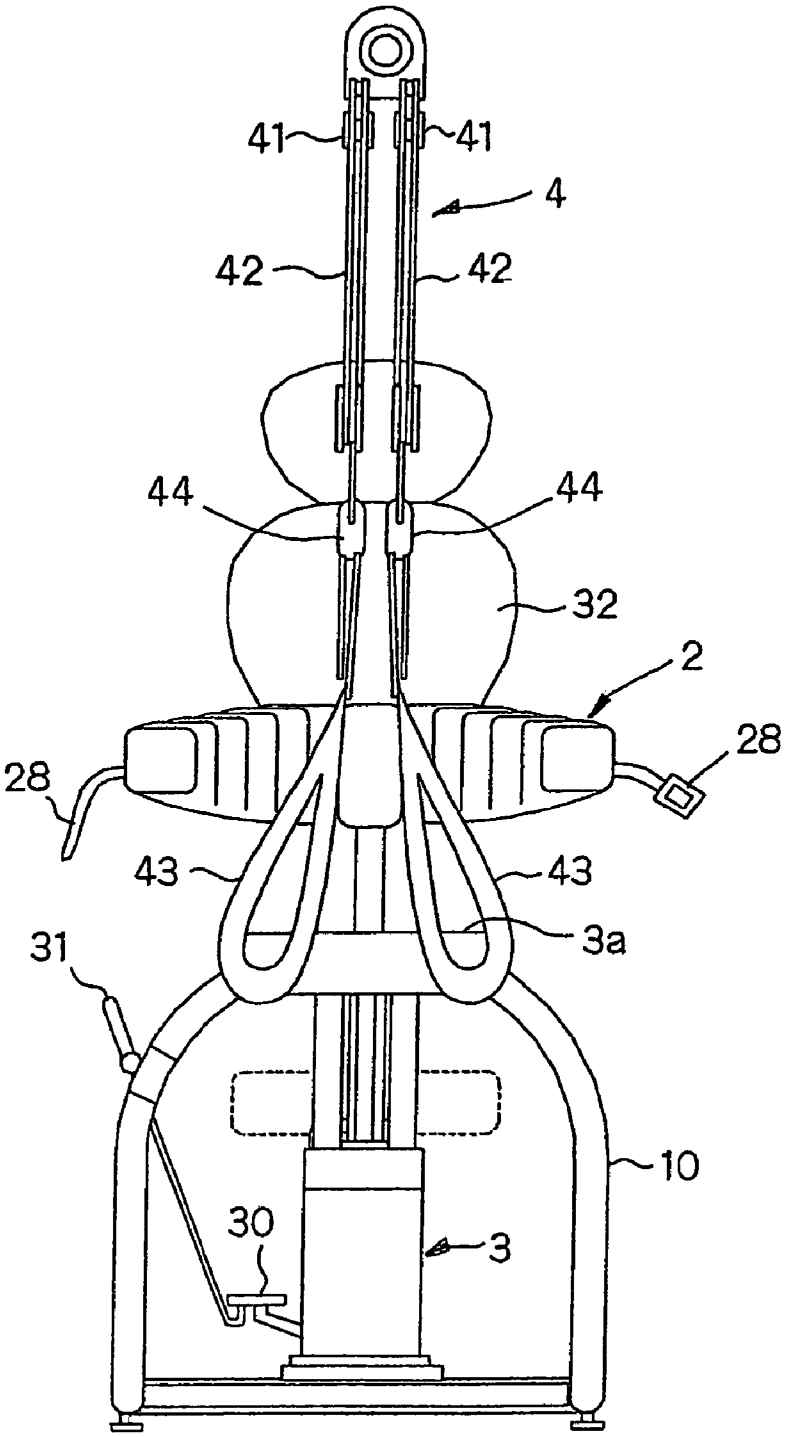
FIG. 18 is a front view illustrating health equipment according to still another embodiment of the present invention.

(3) By constructing the leg hanging unit 4 used in the first embodiment in such a manner that it comprises two units each including a pulley 41, a hanger string 42, a leg holder 43 as shown in FIG. 18, and a stopper 44, the left leg and the right leg of the user can be held by the separate leg holder 43 respectively to carry out mobilization.

In this arrangement, by hanging each leg at the different levels or by moving them alternately, various kinds of stimulation may be applied to the lumber.

Figure 19:
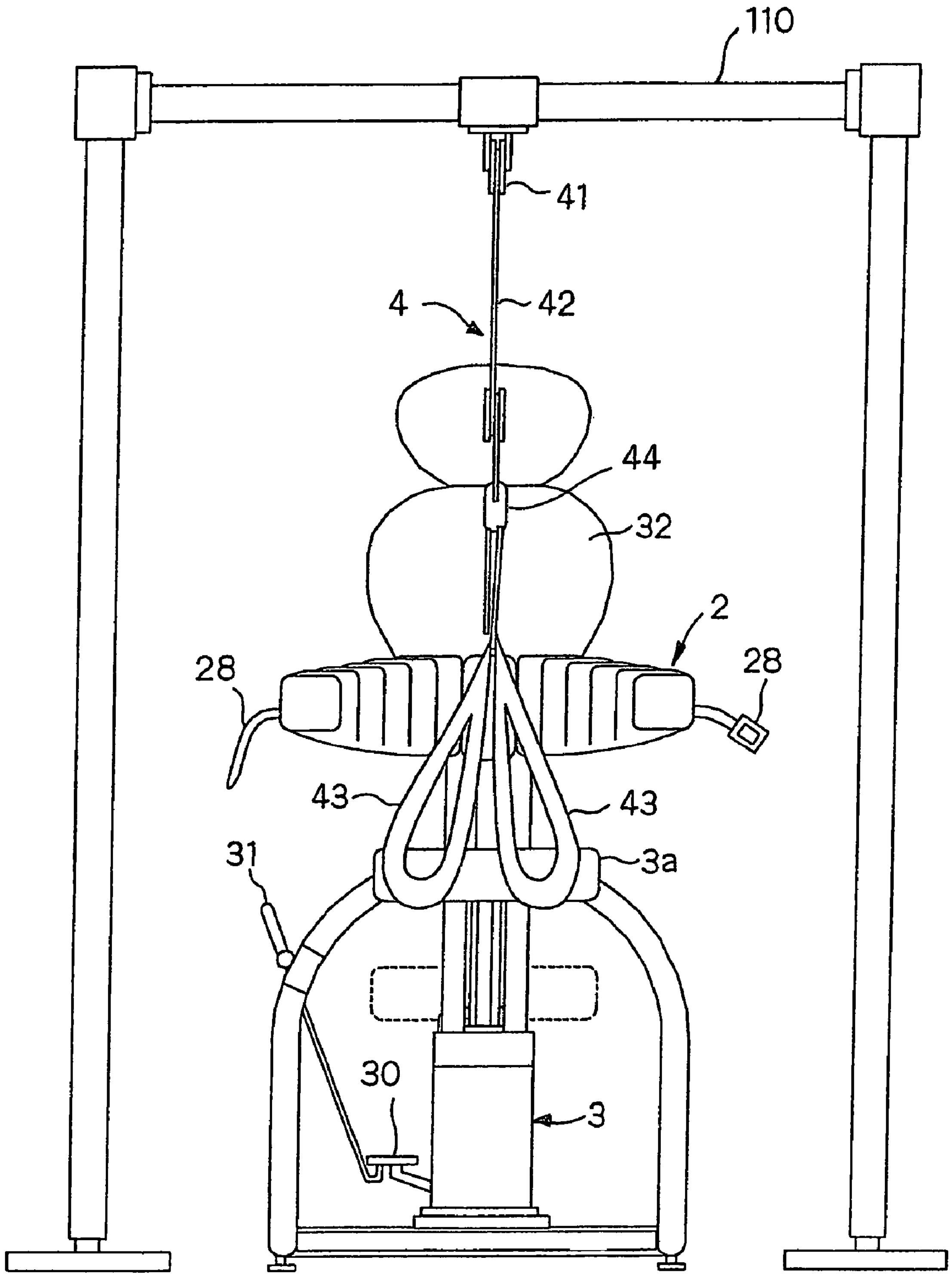
FIG. 19 is a front view illustrating health equipment according to still another embodiment of the present invention.

(4) The supporting body for supporting the leg hanging unit 4 may be formed by a post 110 that is separate from the equipment body 1, as shown in FIG. 19. Likewise, the chin holding unit 5 used in the second embodiment, the shoulder hanging unit 6 used in the third embodiment, and the load applied dragging unit 8 used in the fifth embodiment may also be supported by the supporting post that is separate from the equipment body 1.

Figure 20:
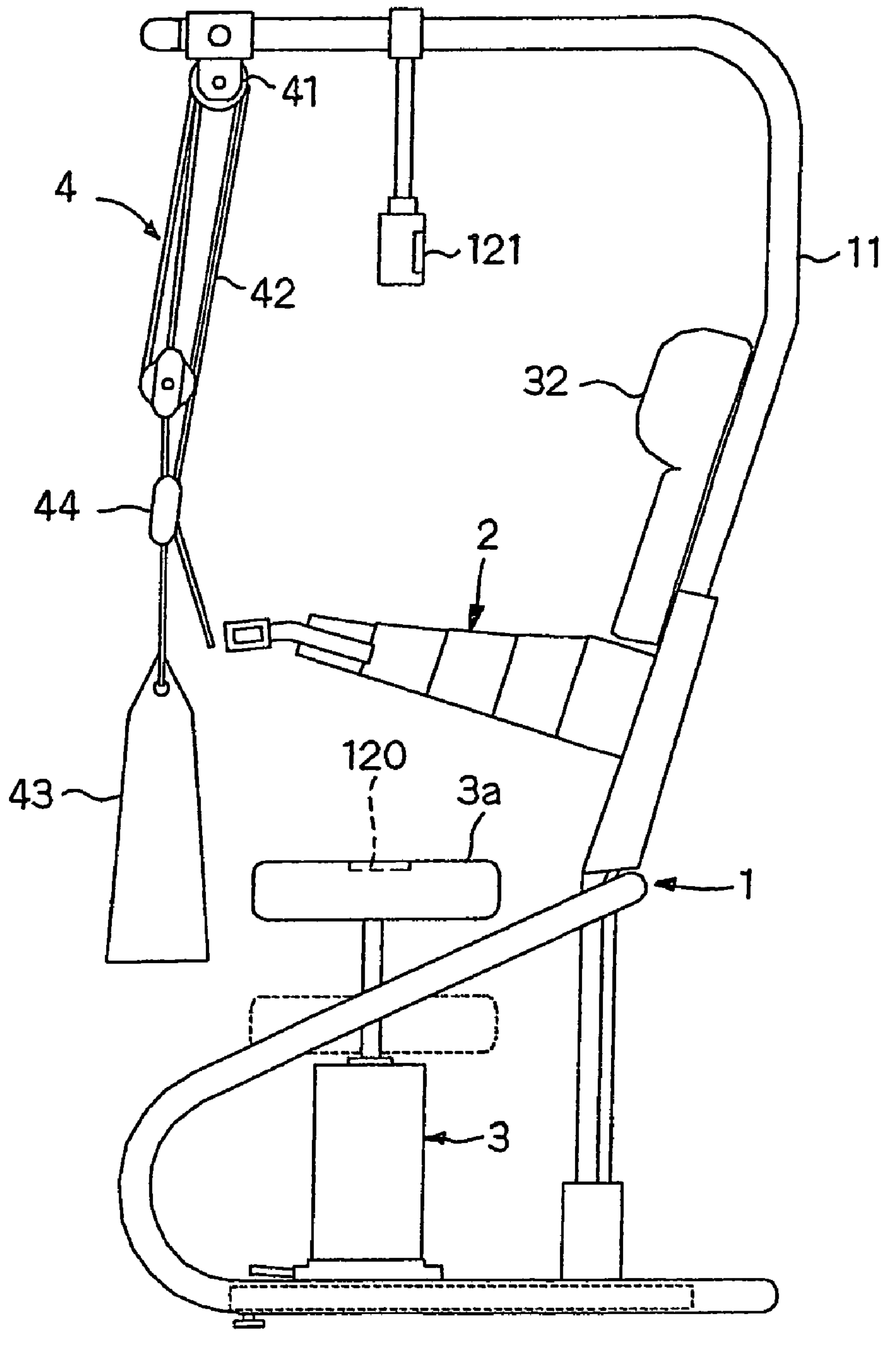
FIG. 20 is a side view illustrating health equipment according to still another embodiment of the present invention.

(5) As shown in FIG. 20, there may be provided a weight detecting sensor 120 on the upper surface of the seat portion 3*a* to detect the weight of the user applied to the seat portion 3*a*. The load applied to the lumber increases in inverse proportion to the weight of the user applied to the seat portion 3*a*. Therefore, the load applied to the lumber may be adjusted based on the weight data detected by the weight detecting sensor 120. The monitor 121 for displaying the weight data may be arranged for example on the post 11 where the user can see.

Figure 21:
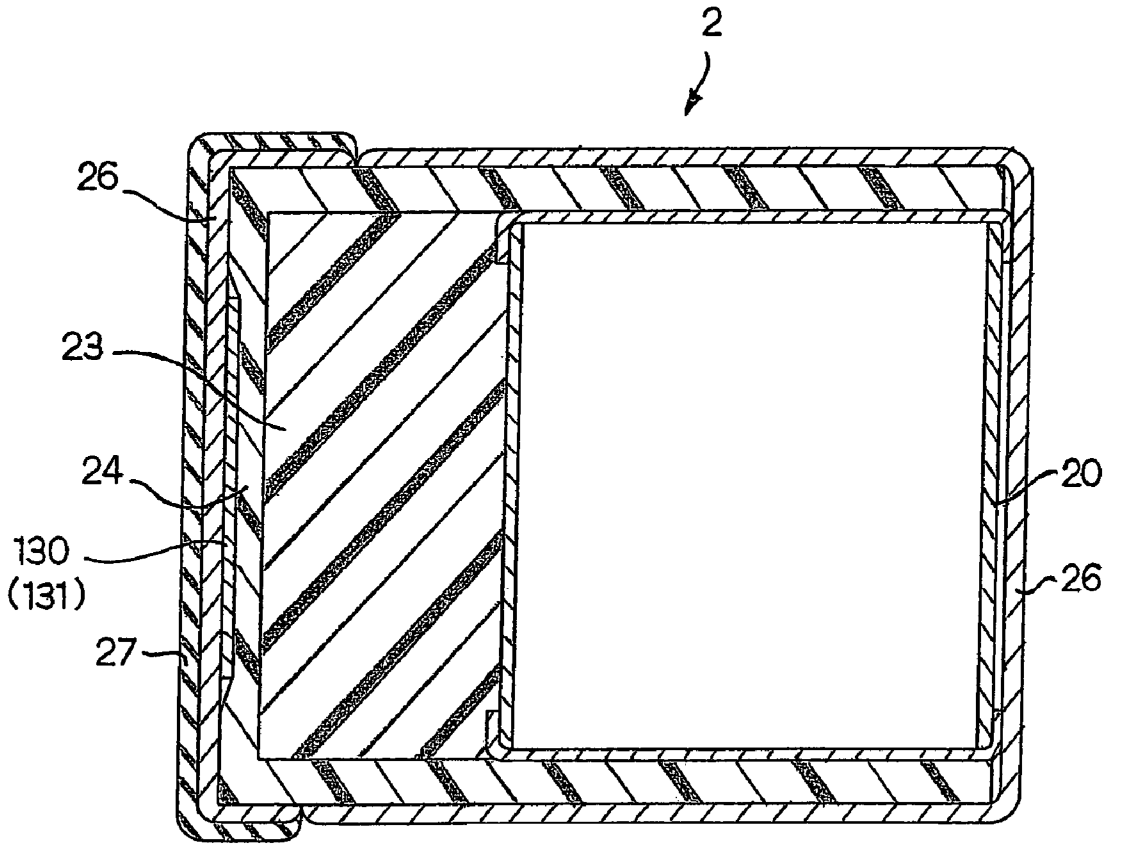
FIG. 21 is an explanatory cross section illustrating health equipment according to still another embodiment of the present invention.

(6) As shown in FIG. 21, a heating means such as a heater 130 may be provided within or on the inner surface of the trunk support 2, so that thermal treatment can be carried out simultaneously with dragging treatment of the lumber.

Alternately, by providing a conductive plate 131 within or on the inner surface of the trunk support 2 and feeding a weak current thereto, low frequency treatment may be carried out simultaneously with dragging treatment for the lumber.

(7) The supporting member 20 constituting the trunk support 2 is not limited to a metallic material, but it may be formed of a hard plastic material or the like. The human body protecting member 23 for the trunk support 2 may be a bag containing liquid such as water or gel instead of a pliant resin material such as urethane resin to improve the feeling of being fitted to the trunk of the body.

(8) An electric mechanism for placing the trunk support 2 onto the trunk of the body automatically may be integrated. It is also possible to integrate an electric mechanism for moving the trunk support 2 or the chair 3 upward and downward automatically.

Figure 22:
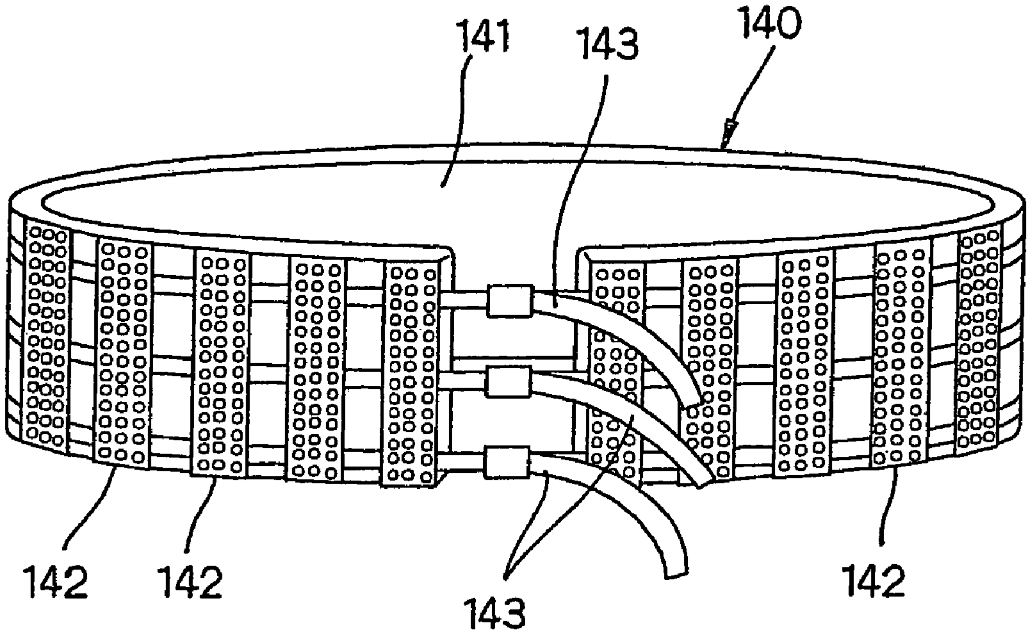
FIG. 22 is a perspective view showing a corset that can be used together with health equipment according to the respective embodiments of the present invention.

(9) The user may wear a corset 140 as shown in FIG. 22 on his or her trunk before placing the trunk support 2. The corset 140 comprises a main body 141 including a flexible belt material for example of urethane resin or the like and a contact member 142 such as an embossed rubber sheet or Velcro fastener or the like adhered on the outer surface thereon, so that the contact member 142 comes into contact with the non-slip member 27 on the trunk support 2 and generates a large contact resistance. On the ends of the main body 141, there are provided fastening belts 143 to be used to wear the corset 140 around the trunk of the body.

(10) Though the present invention is applied to the lumbago treatment equipment in these embodiments, health equipment of the present invention is not limited thereto, but it may be applied to the ancillary equipment for rehabilitation for the disabled people.

INDUSTRIAL APPLICABILITY

As is described thus far, since health equipment of the present invention comprises a bendable trunk supporting means that holds and supports the trunk of the human body so that dragging treatment can be carried out with the trunk of the human body securely supported, it is effective to lumbago treatment.

The invention claimed is:

1. A lumbago treatment apparatus for dragging the lumbar with the weight of the lower part of the body by supporting the trunk of the user, comprising:

an apparatus body;

bendable trunk supporting means fixedly connected to said apparatus body for holding and supporting the trunk of the user from the right and left sides, for fixedly positioning only the trunk of the user to the apparatus body and for immobilizing only the trunk of the user;

a seat portion, being removable or movable in the vertical direction relative to the bendable trunk supporting means, on which the user sits; and leg hanging means for hanging and supporting the legs of the user, the leg hanging means arranged relative to the apparatus body so that the bendable trunk supporting means in combination with the leg hanging means allows suspension of the user's hips with no direct support of the user's hips when the trunk of the user is fixedly positioned against the apparatus body;

wherein said leg hanging means enables the application of a lumbar twisting force by turning the hanging legs of the user rightward and leftward while the trunk of the user is fixedly positioned against the apparatus body.

2. The apparatus of claim 1, wherein said leg hanging means comprises a supporting body, a pulley arranged in connection with said supporting body, a string body suspended from said supporting body by said pulley, and a leg holder mounted to a lower end of said string body for holding the legs of the user, the level of said leg holder being freely adjustable by operation of said string body.

3. The apparatus of claim 2, wherein the position of said leg hanging means with respect to the user is adjustable in forward and backward directions.

4. The apparatus of claim 2, further comprising two hanging units each including said pulley, said string body, and said leg holder respectively.

5. The apparatus of claim 2, wherein said supporting body is a post extending above said trunk support and forward over said seat portion.

6. The apparatus of claim 2, wherein said pulley is adjustable in forward and backward directions relative to said supporting body.

7. The apparatus of claim 2, wherein said pulley is detachably mounted to said supporting body.

8. The apparatus of claim 1, further comprising a leg exercising means for raising and lowering the legs of the user with respect to the user's trunk.

9. The apparatus of claim 8, wherein said leg exercising means comprises at least one leg supporting portion arranged forward of said apparatus body for supporting legs of the user, and a raising/lowering mechanism for raising and lowering said at least one leg supporting portion.

10. The apparatus of claim 9, wherein said at least one leg supporting portion comprises two leg supporting portions and said raising/lowering mechanism raises or lowers said two leg supporting portions simultaneously or alternately.

11. The apparatus of claim 1, further comprising rehabilitation means for carrying out pulling exercise by the movement of the arms, legs, or the upper part of the body of the user relative to the rest of the user's body

12. The apparatus of claim 1, wherein said trunk supporting means includes a trunk support comprising a supporting member in a midsection of said trunk support, a first trunk supporting arm extending from a left side of said supporting member in the midsection and a second trunk supporting arm extending from a right side of said supporting member in the midsection, each of said first and second trunk supporting arms comprising interlinked supporting members, and adjacent ones of said supporting members being rotatably linked to one another.

13. The apparatus of claim 12, wherein each of said supporting members comprises at least one linking member for rotatably linking said supporting member to an adjacent one of said supporting members.

14. The apparatus of claim 13, wherein each of said at least one linking member is connected to an inner edge of the respective one of said supporting member to thereby enable only inward turning of said supporting members.

15. The apparatus of claim 12, wherein each of said first and second trunk supporting arms is arranged to be bendable inwardly toward the user such that said trunk support is positionable around the trunk of the user.

16. The apparatus of claim 12, wherein said supporting members have substantially the same form.

17. The apparatus of claim 12, wherein said trunk support is arranged to be fastened around the trunk of the user.

18. The apparatus of claim 17, further comprising a fastening belt connected to said trunk support for fastening said trunk support around the trunk of the user.

19. The apparatus of claim 1, wherein each of said supporting members is arranged to support a portion of the back of the user or a portion of the belly of the user from the right or left side such that one of said supporting members at one end of said trunk support is arranged to support the belly from the left side, another one of said supporting members at an opposite end of said trunk support is arranged to support the belly from the right side and said supporting member in the midsection is arranged to support the back of the user.

20. Lumbago treatment using the apparatus of claim 1, wherein:

said means for supporting the trunk of the user and immobilizing the trunk of the user by said trunk support means is fixedly connected to said apparatus body, whereby said lumbago treatment comprises:

supporting and immobilizing the trunk of the user to the apparatus body so as to allow suspension of the hip of the user in the air with no vertical support beneath the hip;

raising the knees or ankles of the user upwardly and maintaining the legs of the user in a hanging state by said leg hanging means; and applying a lumbar twisting force by turning the hanging legs of the user rightward and leftward while the trunk of the user is fixedly positioned against the apparatus body.

21. A lumbago treatment apparatus for dragging the lumbar with the weight of the lower part of the body by supporting the trunk of the user, comprising:

an apparatus body;

bendable trunk supporting means fixedly connected to said apparatus body for holding and supporting the trunk of the user from the right and left sides, for fixedly positioning only the trunk of the user to the apparatus body and for immobilizing only the trunk of the user;

a seat portion, being removable or movable in the vertical direction relative to the bendable trunk supporting means, on which the user sits; and leg hanging means for hanging and supporting the legs of the user, the leg hanging means connected to the apparatus body so that the bendable trunk supporting means in combination with the leg hanging means allows suspension of the user's hips with no direct support of the user's hips when the trunk of the user is fixedly positioned against the apparatus body;

wherein said leg hanging means enables the application of a lumbar twisting force by turning the hanging legs of the user rightward and leftward while the trunk of the user is fixedly positioned against the apparatus body.

* * * * *